(12) United States Patent
Navarro Aviño

(10) Patent No.: US 7,700,828 B2
(45) Date of Patent: Apr. 20, 2010

(54) BIOLOGICAL CONTAMINATION-REMOVAL METHOD

(76) Inventor: Juan Pedro Navarro Aviño, Jativa, 3 d36, Valencia (ES) 46002

( * ) Notice: Subject to any disclaimer, the term of this patent is extended or adjusted under 35 U.S.C. 154(b) by 276 days.

(21) Appl. No.: 10/551,013

(22) PCT Filed: Apr. 2, 2004

(86) PCT No.: PCT/ES2004/000151

§ 371 (c)(1),
(2), (4) Date: Sep. 29, 2005

(87) PCT Pub. No.: WO2004/087861

PCT Pub. Date: Oct. 14, 2004

(65) Prior Publication Data

US 2007/0083942 A1    Apr. 12, 2007

(30) Foreign Application Priority Data

Apr. 2, 2003    (ES) ................ 200300857

(51) Int. Cl.
*A01H 5/00*    (2006.01)
*C12N 15/09*   (2006.01)
*C12N 15/82*   (2006.01)

(52) U.S. Cl. ................ 800/278; 800/298; 800/294; 435/468

(58) Field of Classification Search ........ None
See application file for complete search history.

(56) References Cited

U.S. PATENT DOCUMENTS 6,080,915 A * 6/2000 Gordon et al. ............ 800/300
6,455,761 B1   9/2002 Kuvshinov et al.
6,576,816 B2 * 6/2003 Terry et al. ............... 800/306

FOREIGN PATENT DOCUMENTS

WO    WO 00/71695    11/2000

OTHER PUBLICATIONS

Gisbert et al. Biochemical and Biophysical Research Communications (2003) 303:440-445.*
Gisbert et al. International Journal of Phytoremediation (2008) 10:1-12.*
Mason, Hugh S. et al, Expression of Norwalk virus capsid protein in transgenic tobacco and potato and its oral immununogenicity in mice. Proc. Natl. Acad. Sci. USA, vol. 93., pp. 5335-5340, May 1996.
Rodriguez-Garcia, Cecilia M. et al, Transfer of the yeast gene SKI2 to tobacco. NOTA en Agrociencia 36:675-681, 2002.
Sathiyamoorthy, P. et al, Heavy metals in medicinal and fodder plants of the Negev desert. J. Environ. Sci. Health. A32(8), 2111-2123 (1997).

* cited by examiner

*Primary Examiner*—Medina A Ibrahim
(74) *Attorney, Agent, or Firm*—Defillo & Associates, Inc; Evelyn A. Defillo

(57) ABSTRACT

The invention relates to a transgenic wild type plant species from *Nicotiana glauca* transformed with the phytochelatin synthase TaPCS gene from wheat for the phytoremediation of soils contaminated with heavy metals and other pollutants.

8 Claims, 1 Drawing Sheet

BIOLOGICAL CONTAMINATION-REMOVAL METHOD

BACKGROUND OF THE INVENTION

1. Field of the Invention

This invention is of application in the metal elimination that contaminates soils and aquatic zones.

2. State of the Art

At present, the state of the art provides alternative ways of solving the problem. The most habitual are also the costliest and they base on, fundamentally chemical and physical methods, as they are: the committal of the contaminated soils with inert materials, the cleanliness "in situ" with the machines and chemical suitable material, the storage as poisonous residues in the places regulated for it (with correspondent license), etc.

In the United States there have been carried out experiences of recovery of the contaminated soils, using natural plants, of the type of the corn, tomato, sunflower, *Brassica juncea*, etc., and trees principally willow and black poplar. Most of these pioneering experiences has been realized by the American army moved by the desire to recover soils been contaminated with the metallic garbage that provoke the bullets that are in use in the tests of shot. These metals contain fundamentally lead.

Also another type of experiences have been performed in New Jersey. It was carried out a selection of cultures of *Brassica juncea* (*Brassica juncea* (L) Czem) with aptitude to accumulate the elected metals; it was used enmendants of the soil or chelants substances. Later they allowed them to glow, and to be harvest, and the contain in metals have been analyzed. In these two cases, the used techniques have been fundamentally: treatment of contaminated soils, and regeneration by metal accumulation in the cultivated plants. The "U.S. Environmental Protection Agency", also acquaintance as EPA, has been the pioneering institution in the study of these processes of phytoremediation. Together with the company "Phytotech" was the manager of realizing the mentioned process of recovery of the contaminated soils in New Jersey. In the experiments in which the objective has been the recovering of munition, as the one mentioned above, it has participated actively the engineers' body of the American army (Army Corps of Engineers). The company Phytotech is one of pioneers in the whole world. In Spain there exist references of ELECNOR, which it applies technologies of bioremediation patented by the North American company ECS.

Some examples of vegetable used material:

hybrid trees of black poplar have been in use for extracting nickel, cadmium and zinc of contaminated soils (University of Georgia, USA, "Savannah River Ecology Laboratory").

In the department of energy of Ashtabula, Ohio, plants of sunflower have been in use for remediation of soils and waters contaminated by uranium.

Some examples of important patents are the following ones:

U.S. Patent. Phytorecovery of metals using seedlings. U.S. Pat. No. 911,655, Aug. 15, 1997, Phytotech, Inc. (Monmouth Junction, N.J.).

U.S. Patent. Method of using *pelargonium* sp. as hyperaccumulators for remediating contaminated soil. U.S. Pat. No. 185,797, Nov. 4, 1998, University of Guelph (Guelph, Calif.).

U.S. Patent. Methods for removing pollutants from contaminated soil materials with a fern plant. U.S. Pat. No. 546,941, Apr. 11, 2000, University of Florida (Gainesville, Fla.). The invention describes the use of a variety that is less extensive geographically that *N glauca*. It is a question of a fern that basically accumulates enormous quantities of arsenic. Methods are described to carry out the decontamination using one or different varieties of ferns. The use of this type of plants has fundamentally the disadvantage of which there is located in very humid habitats which limits his use. Besides the need to receive very much water contribution can have negative effects for the soil where they grow since, on having contributed big quantities of water, this one can displease the metals at deeper levels or spread them.

Since it parts with the information contributed in the exposed patents, the work it has centred on processes of bioremediation, especially using hyperaccumulators (those plants that possess an extraordinary capacity of absorption of metals, and of accumulation in his biomass).

The phytoremediation consists basically of the use of plants or of vegetable material, to decontaminate soils with high concentrations of harmful elements. Recently a review has been realized, about the topic, by two Spanish investigators, in the publication: "Phytoextraction: to cost-effective plant-based technology for the removal of metals from the environment". Carlos Garbisu, Itziar Alkorta. Bioresource Technology 77 (2001) 229-236. Where the state of the investigation is described in phytoremediation, topcoat being based on the concrete aspect of the phytoextraction.

One key article (review), for the importance of the works realized by the authors are the followings:

Chaney, R. L., Malik, M., Li, Y. M., Brown, S. L., Brewer, E. P., Angle, J. S., Baker, A. J. M., 1997. Phytoremediation of soil metals. Current Opin. Biotechnol. 8, 279-284.

Salt, D. E., Smith, R. D., Raskin, I., 1997. Phytoremediation of soil metals. Current Opin. Biotechnol. 8, 279-284. This is an article of reference for the punctual contribution and Corn and buckthorn are two species that accumulate lead. (Huang, J. W., Cunningham, S. D., 1996. Lead phytoextraction: species variation in lead uptake). As for the cadmium, *Salix viminalis, Thlaspi caerulescens* and *Alyssum murale* seem to be the best species (*SALIX* EXPERT PHYTOEXTRACTOR, Maria Greger, Dept of Botany, Stockholm University, S-106 91 Stockholm, Sweden).

Concerning to the molecular biology of metal absorption, fundamentally researchers have worked with plants of the genre of *Brassica*, and among them especially *Brassica juncea*. In these type of plants genetic transformations have been realized by means of skills of biotechnology. Also they have been carried out in another type of vegetable varieties as black poplar and certainly *Arabidopsis*. Regarding the genes that have been in use for decontaminating heavy metals, it is necessary to distinguish basically three families: metallothioneins, phytochelatins, and genes that regulate the processes of oxidation-reduction. It is necessary to emphasize the pioneering work realized with bacterial genes that are specialized in the absorption of mercury, which marked a milestone in this field: Rugh, C. L., Wilde, H. D., Stack N. M., Thompson, D. M., Summers, A. O., Meagher, R. B., 1996. "Mercuric ion reduction in transgenic *Arabidopsis thaliana* plants expressing to modified bacterial mere gene". Proc. Natl. Acad. Sci. USA 93, 3182-3187.

The most important works in this field, apart the mentioned one, have been carried out by Schroeder, Rea, and Therry. During the same year, Schroeder studied for the first time the enzyme produced by the gene TaPCS1, which is a phytochelatin of wheat. (The EMBO Journal Vol. 18 Not 12 pp. 3325-3333, 1999. "Tolerance to toxic metals by to gene family of phytochelatin synthases from plants and yeast". Stephan Clemens, Eugene J. Kim, Dieter Neumann and Julian I. Schroeder). The second one cloned, the homolog phytochelatin of *Arabidopsis* (Proc. Natl. Acad. Sci. USA, Vol. 96, pp. 7110-7115, June 1999). "AtPCS1, to phytochelatin synthase from *Arabidopsis*: Isolation and in vitro reconstitution". Olena K. Vatamaniuk, Stéphane Mari, Yu-Ping Lu, and Philip A. Rea). And the third one transformed in several occasions, *Brassica juncea* with genes that increase the metal absorption ("Cadmium Tolerance and Accumulation in Indian Mustard Is Enhanced by Overexpressing γ-Glutamylcysteine Synthetase". Yong Liang Zhu, Elizabeth A. H. Pilon-Smits, Alice S. Tarun, Stefan U. Weber, Lise Jouanin, and Norman Terry. Plant Physiology, December 1999, Vol. 121, pp. 1169-1177).

SUMMARY OF THE INVENTION

When a place is contaminated with heavy metals, it can be the origin of a serious problem of environmental health and even of human health. The metals can happen to be dissolved in the water of rivers or source of water nearby, and also they can happen to be absorbed by plants or trees, giving place at its entry in the nourishing chain. Even, not happening any of these two processes, the metal can be accessible to any alive being that accidentally manipulates the waters or contaminated soils. Sometimes, there takes place such a serious problem of pollution (as it happened with the company Boliden, in the Aznalcollar region in the year 99), that the metals devastate the flora and fauna that they find to its step. It emerges therefore, a technical problem that consists of the manipulation of these contaminated places, either in order that they are not a danger for the environment, or in order that they are returned to his natural state before being contaminated.

The present invention provides a procedure to decontaminate a media of growth contaminated with metals, using individuals of the plant species *Nicotiana glauca*, and *Nicotiana glauca* modified genetically (for inclusion of the gene TaPCS1), during a period of sufficient time in order that the metals are absorbed by the roots and accumulated in the different tissues of the plant (root, stem, leaves). Being the metals of a group consisting of lead, arsenic, cadmium, copper, mercury, iron, chromium, uranium, nickel and zinc.

The proposed procedure uses the plant species *Nicotiana glauca*, chosen of a group of vegetable surviving species in a contaminated area, located in Valencia city.

At present, the state of the art provides alternative ways of solving the problem. The most habitual are also the costliest and they base on fundamentally chemical and physical methods, since they are: the committal of the soils contaminated with inert materials, the cleanliness "in situ" with the machines and chemical suitable material, the storage as poisonous residues in the places adapted for it (with license), etc. All these skills have the big disadvantage, of their high cost, in addition to which in any cases it is not possible to carry out the finished cleanliness. The committal, it does not look like a real solution to the problem, but rather a postponement of the same one in the time. The same might be said, of the storage of the soils contaminated in the places conditioned for it.

The techniques that use hyperaccumulator plants have the great disadvantage of which these plants possess some characteristics that dissuade them as solution, namely: low biomass, adjustment to a very concrete habitat, normally only accumulate a specific metal while they do not resist a set of diverse metals, and have a short cycle of life. What is looked actually, is that the plants absorb the metal pollutant (or the set of metals pollutants), and that they transport it to the parts able to be collected. Later this material would be harvested and it would arrange suitably or would burn itself (also it might study other alternatives).

In the current state of the art, since it has been mentioned previously, it has been elected another type of plants different from the hyperaccumulators, among them it is necessary to stand out on every *Brassica juncea*. Later, on these plants there have introduced genes that they qualify the plant species to a better response. In general, the use of the biotechnology to solve this type of problems of pollution, has the clear disadvantage of the enormous consumption of time that is needed to solve the problem, and that besides the process of decontamination has to be carried out almost always "in situ". Nevertheless, the phytoremediation (disciplines that use vegetable material to decontaminate contaminated places), it is always a much less costly procedure in terms of money.

In the present invention, one manages to improve the state of the art previously developed. In this way:
 1.—Wild chosen flora: it is adapted to specific climatology and edaphology
 2.—It is very competitive ("weeds") in "normal" situations and of metal excess.
 3.—Adapted to soils of low nutritional and water content (they resist water and nutritional stress).
 4.—Improved natural capacity. It means that it is probable that they are individuals modified genetically with regard to those who grow in not contaminated zones.
 5.—Improved capacity by means of genetic modification. There has been introduced a gene of wheat, which level of expression is permanently increased. The result is a major capacity of absorption of heavy metals, as Pb, Cd, etc.

The point one, it does not mean that these plants are not a transportable technology to other points of the world geography. Probably the opposite will happen, since one the advantages of the used plant species is that it survives habitually in extensive geographical areas of the world. This way for example, although it is original of the south and central part of the American continent, it spreads also over all United States and Canada, the whole Australian continent, and part of Europe and Japan. Besides, this plant species reproduces by cuttings, it replicates with facility in the field, provides abundant seeds, has aptitude to banish animals (which is a guarantee of his difficulty to enter the feed chain), is in use as ornamental plant in the United States and Canada, and all that together with the familiar beneficial characteristics for phytoremediation as they are: deep root system, high biomass, and adjustment to soils nutritionally low and of high pollution for metals. Another additional, not despicable advantage exists still, and the fact is that the technology of transformation of genes to vegetable species is limited to a limited group of plant species, among them the plant species that the investigators more have worked is *Nicotiana tabaccum*. Therefore, *Nicotiana glauca*, might benefit from the whole scientific technological undivided assets that has developed for *Nicotiana tabaccum*.

In addition to the importance that has the vegetable species that has been chosen to be biotechnologically modified, it is necessary to emphasize the importance of the gene that has been transferred. The gene TaPCS1, it was studied in depth demonstrating a great specialization and yield in the absorption of lead and cadmium in yeast (used like model system). It was the first phytochelatin synthase that was studied, and it belongs to one vegetable species that is cultivated habitually in the exterior of the laboratories (it does not happen equally with *Arabidopsis*), what it could mean a better capacity of adjustment to the external environment. This gene had never been transformed into plant previously, hence the innovation and importance of this fact.

The importance of the role played by the phytochelatins in the detoxification and homeostasis of heavy metals, is still today an object of discussion. Recent works have shed some light in the molecular base of this process and also in the role of the phytochelatins and the phytochelatin synthases in the process of metal accumulation. Nevertheless part from the described investigation very recently it is incoherent with previous works and it needs an urgent clarification.

Phytoremediation and Metal-Binding Peptides

In the last decades the concern for the global Earth environment has impulse a major research focus in decontamination. The phytoremediation is an emerging and low cost technology that utilizes plants to remove, transform or stabilize toxic chemicals located in water, sediments or soils. Physiological studies indicate that heavy metal tolerance is one of the prerequisites of heavy metal hyperaccumulation in plants (Kramer et al., 1997; Raskin et al., 1997). Phytoremediation of heavy metals more likely require genetic engineering metal tolerance in selected wild plant species, which are fast-growing, of high biomass, and tolerant to a wide range of environmental conditions.

Living organisms have developed molecular processes that allow cells the capability to detoxify (in some particular concentration ranges) heavy metals. In eukaryotic cells, these mechanisms include mainly sequestration and chelation by specific ligands. Among these kind of molecules most of researchers interest has been focused in the last years in two of them: metallothioneins and phytochelatins. Metallothioneins are ubiquitous low molecular weight proteins and polypeptides of extremely high metal and sulfur content (Kägi J. H. and Schaffer A., 1988). Phytochelatins (PCs) are thiolate peptides with the primary structure $(\gamma\text{-Glu-Cys})_n$-Gly, (where n=2-11) non-translationally synthesized from glutathione (Grill, E. et al. (1989). PCs have been identified in a wide variety of plant species including monocots, di-cots, gymnosperms and algae (Rauser, 1999).

GSH is Substrate of Phytochelatin Synthase.

PCs are synthesized from Glutathione (GSH). GSH is synthesised in a two-step pathway (FIG. 1) catalysed by γ-glutamylcysteine synthetase (γ-ECs) and glutathione synthetase (GS); requires energy since both are ATP-dependent enzymes. The level of GSH decreases on the induction of PCs in plant cell cultures and the exposure of whole plants or plant cell cultures to an inhibitor of GSH biosynthesis, buthionine sulfoximine (BSO), also inhibits the induction of PCs and/or confers hypersensitivity to metal ions. Furthermore, in cell cultures the effects of BSO can be reversed by the addition of GSH evidencing a marked interaction between GSH and phytochelatin biosynthesis regulation.

The Key Role of PCs in Heavy Metal Tolerance is Discussed

What is the role played by PCs in heavy metal (HM) tolerance and accumulation? Do they are essential instruments in engineering phytoremediation? Do they play a basic role in plants that emerge more tolerant by natural selection under HM pressure? Most significant recent advances in the understanding of the general role played by PCs comes from molecular genetic studies using different plant and fungi model systems. Specially for the differential metal tolerance observed among naturally occurring selected plants, resistant and sensitive ecotypes.

Negative Evidence

Some researchers think that previous studies of phytochelatin production in response to Cd and Cu demonstrated that PCs are not responsible for metal tolerance although they are indeed involved in the detoxification process. This affirmation relays upon the fact that root tips of Cd-tolerant plants of *Silene vulgaris* exhibit a lower rate of phytochelatin production accompanied by a lower rate of longer chain phytochelatin synthesis than those of Cd-sensitive plants *Silene vulgaris* (De Knecht, et al. 1994). Regarding their role in naturally selected plants that have increased HM accumulation, some researchers believe that the investigation of tolerant *Silene vulgaris* plants from the copper mining dump shows that PCs are not responsible for the development of the heavy metal tolerant phenotypes. This is based in the fact that Cd- and Cu-complexes disappear in the roots of water cultures of *Silene vulgaris* between 7 and 14 days after heavy metal exposition. Although the binding of HM ions to PCs exists it seems to play only a transient role in the heavy metal detoxification mechanism of this plant species (Leopold, et al. 1999). Similar findings have been reported for the hyperaccumulator *Thlaspi caerulescens* and the related non-accumulator *T. arvense*. Total PC levels found in the hyperaccumulator were generally lower respect to the non-accumulator, despite correspondingly higher metal concentrations. However again, similarly to *Silene vulgaris*, PCs were produced by both species in response to Cd, and phytochelatin levels showed a similar positive correlation with Cd-concentration in leaf and root tissues (Ebbs, et al. 2002). What are the molecular bases of PCs enzymatic regulation for this apparent absence of relevance in HM tolerance? Although Cd-tolerant *Silene vulgaris* plants produce three times less PCs than Cd-sensitive ones, when are exposed to external supply of Cd, neither the PCS activity nor PC degradation accounts by for the difference in PCs concentration (De Knecht, et al. 1995). Therefore, all these evidences may suggest a lack of importance for the PCs role in *Silene vulgaris* and *Thlaspi caerulescens* respect to Cd tolerance. Consequently, from all this information some researchers have concluded that differential synthesis of PCs is not involved in producing differential metal tolerance. However it also can be argued that PCs concentration is three times higher in Cd-sensitive *Silene vulgaris* plants after external Cd supply respect to the non sensitive, therefore whether they really play a key role or not in these sensitive plants should be questioned.

Very recently a set of evidences against the possible central role of PCs in HM detoxification have been presented. When *Arabidopsis thaliana* PCS gene (AtPCS1) was overexpressed with the goal of increasing PC synthesis and therefore metal accumulation, transgenic lines showed paradoxically hypersensitivity to Cd. However, this hypersensitivity disappeared when GSH was supplemented in the medium. Consequently, it is argued that Cd hypersensitivity seems due to the toxicity of PCs, as they existed at supraoptimal levels when compared with GSH levels (Lee, S. et al. 2003).

Positive Evidence

The first evidence comes from two basic facts: plant cells when exposed to HM rapidly accumulate PCs and PCs production is activated by HM ions (Grill et al., 1989). When the activity of the partially purified enzyme was determined in vitro, the enzyme was active only in the presence of HM ions (being Cd the best activator). When the activity was determined in vivo (in both intact plants and plant cell cultures), HM also induced PC biosynthesis (Rauser, 1995). Lack and restoration of function has been also an important source of evidences. For example, it was reported that phytochelatindeficient *Saccharomyces pombe* and *Arabidopsis thaliana* mutants are hypersensitive to Cd. Furthermore, AtPCS1 was able to suppress the Cd-sensitive phenotype in Brewer's yeast (Vatamaniuk, et al., 1999). Stronger evidence however, has come from a wheat cDNA, TaPCS1, whose expression in *S. cerevisiae* results in a dramatic increase in Cd tolerance (Clemens, et al., 1999). This work demonstrated that TaPCS1 expression led to an augment in $Cd^{2-}$ accumulation inside the yeast cells even at concentrations that do not affect the growth. More important, this group showed that heterologous expression of PCS genes is sufficient to confer enhanced metal tolerance. Performing growth assays with *S. cerevisiae* cells expressing AtPCS1 and SpPCS (*S. pombe* homolog), they have demonstrated that phytochelatin synthesis alone can significantly increase cellular Cd tolerance. Besides, when wheat roots were investigated for TaPCS1 expression, RT-PCR experiments indicated that this PCS expression is constitutive and enhanced by Cd, consistent with the reported constitutive activity of PCS (Grill, et al., 1989) in roots and stems (Chen, et al., 1997) and coherent with the suggested requirement for organisms to express metal tolerance genes constitutively (Zenk, 1996). Therefore PCS activity is regulated transcriptionally and post-transcriptionally by HM. Are these evidences strong enough to answer the question of whether PCs are essential for HM tolerance? There are now more observations supporting the idea of a key role of PCs in HM tolerance. Very recently the overexpression of gene TaPCS1 in *Nicotiana glauca* selected in a contaminated environment increases Cd tolerance and furthermore lead accumulation. Roots growth was improved drastically (near 160%) and leaves were bigger and greener in the transformed plants respect to wild type, in the presence of 50 μM Cd and even 0.8 mM lead. TaPCS1 transformed plants are able to growth in mining soils having as high as 1572 ppm of lead (2602 ppm of Zn), and accumulating twice lead level than wild type plants. TaPCS1 enhanced expression triggered a higher lead transport (around 200% accumulation) to the root tissue and to the aerial parts (near 150%). Furthermore this improved metal tolerance might be a first step towards engineering hyperaccumulation in this fast-growing, high biomass plant species (Gisbert, et al., 2003). All these positive evidences together strongly suggest that indeed PCs play a role of physiological and ecological relevance in this plant species and many other organisms beyond the manifest role of PCs in HM detoxification.

PCs are Basic Instruments in HM Tolerance, at Least in Some Organisms

A set of evidences has questioned the role played by PCs in HM detoxification. Differential Cd tolerance in *S. vulgaris* in tolerant and sensitive ecotypes is not affected by differential PC production per se. Increased Cd tolerance does not result from an increased accumulation of PCs, from a faster synthesis of longer PCs (forming more stable complexes than shorter forms), or from an increased incorporation of sulfide into PC-Cd complexes in the roots (which likely increases the stability and the potential amount of metal bound per unit of PC-SH). However, tolerant plants reach the same PC concentration as sensitive plants when exposed to higher Cd concentrations. Since the difference between the amounts of PCs induced neither is caused by a difference in the specific PCS activity, nor the rate of PC breakdown, it might then result from a lower Cd concentration in the cytosol caused by a faster transport of PC-Cd complexes, across the tonoplast into the vacuole (Salt, and Rauser, 1995). It also is possible, that tolerant plants contains a higher proportion of acid-soluble Cd, which is not bound to PCs or another complex in addition to PC-Cd is into the vacuole, or that the Cd ion itself is transported via the tonoplast antiporter activity (Salt, and Wagner 1993). Same arguments might likely explain the similar PC concentrations for *T. caerulescens* and *T arvensis*. Nevertheless it is interesting to note that the accumulator *T. caerulescens* produces a positive Cd gradient across the plant from roots to leaves (1000-3000 ppm) while *T arvensis* develops a higher but negative Cd gradient (7500-1000 ppm). Consequently, and following the same accumulation pattern in both *Thlaspi* species, shoot Cd and PC levels are higher in absolute values for *T. caerulescens*, and accordingly PCS showed a less rate of saturation for this ecotype in leaves. Consistently, in this tissue a higher ratio of Cd to γ-GluCys subunits has been observed for *T. caerulescens* as if Cd were preferentially sequestered as high molecular weight complexes (Ebbs, S. et al., 2002). Although these arguments might also contribute to understand the hypersensitivity reported by AtPCS1 overexpression in *Arabidopsis*, evidences are clearly contradictories with previously reported works (Vatamaniuk, et al. 1999; Clemens, et al., 1999). Perhaps, nonspecific protein-protein or others unknown interactions caused by the modification of the AtPCS1 C-terminal region by the FLAG epitope (DYKDDDL) used for protein recognition, may contribute to the observed Cd hypersensitivity in lines overexpressing AtPCS1 (Lee, et al. 2003). The C-terminal domain clearly has some role in PCS activity since the cad1-5 mutant synthesizes a truncated polypeptide predicted to lack nine of the 10 Cys residues in this C-terminal domain, producing an altered phenotype. It is likely that this domain acts as a local sensor by binding heavy metal ions (presumably via the multiple Cys residues, but possibly also others) and bringing them into contact with the activation site in the catalytic domain (Cobbett, C. S., 2000). Therefore, a possible negative interference of AtPCS1 C-terminal FLAG region with PC homeostasis should not be discarded. Beyond of what be the possible explanation for this Cd hypersensitivity, the facts are that after addition of a plant-specific phytochelatin chemically synthesized and, more important, after AtPCS1 expression in mammalian cells, the transfected cells exhibited production of plant-specific PC and higher resistance to $Cd^{2+}$ (Takagi, et al., 2003). It is known that mammalian cells can not synthesize PC because of their lack of PCS.

The work reported specially by Clemens et al., 1999, Tagaki et al., 2003 and, very recently, by Gisbert et al., 2003 have presented solid and consistent evidences for a primary role of PCs in HM tolerance and detoxification in a wide range of organisms. Perhaps negative evidences accumulated might possibly indicate that PCs are essential but not the solitary essential component of the more complex mechanisms developed by organisms to detoxify HM. Consequently other basic elements, when increased or more effective, might reduce the need of a significant augment of PCs and PCS concentrations in such specific cases.

REFERENCES FOR THIS PARAGRAPH

Krämer, U. et al. (1997) The role of metal transport and tolerance in nickel hyperaccumulation by *Thlaspi goesingense* Halacsy. *Plant Physiol.* 115, 1641-1650

Raskin, I., et al. (1997) Phytoremediation of metals: using plants to remove pollutants from the environment. *Curr. Opin. Biotechnol.* 8, 221-226

Kägi J. H. and Schaffer A. (1988) Biochemistry of metallothionein. *Biochemistry* 27, 8509-8515

Grill, E. et al. (1989) Phytochelatins, the heavy-metal-binding peptides of plants, are synthesized from glutathione by a specific γ-glutamylcysteine dipeptidyl transpeptidase (phytochelatin synthase). *Proc. Natl Acad. Sci. USA* 86, 6838-6842

Rauser, W. E. (1999) Structure and function of metal chelators produced by plants; The case for organic acids, amino acids, phytin and metallothioneins. *Cell. Biochem. Biophys.* 31, 19-48

De Knecht, J. A. et al. (1994) Phytochelatins in Cadmium-Sensitive and Cadmium-Tolerant *Silene vulgaris*. *Plant Physiol.* 104, 255-261

Leopold, I. et al. (1999) Phytochelatins and heavy metal tolerance. *Phytochemistry* 50, 1323-1328

Ebbs, S. et al. (2002) Phytochelatin synthesis is not responsible for Cd tolerance in the Zn/Cd hyperaccumulator *Thlaspi caerulescens*. *Planta* 214, 635-640

De Knecht, J. A. et al. (1995) Synthesis and degradation of phytochelatins in cadmium-sensitive and cadmium-tolerant *Silene vulgaris*. *Plant. Sci.* 106, 9-18

Lee, S. et al. (2003) Overexpression of *Arabidopsis thaliana* phytochelatin synthase (AtPCS1) paradoxically leads to hypersensitivity to cadmium stress. *Plant Physiol.* 131, 656-663

Rauser, W. E. (1995) Phytochelatins and related peptides: structure, biosynthesis, and function. *Plant Physiol.* 109, 1141-1149

Vatamaniuk O. K. et al. (1999) AtPCS1, a phytochelatin synthase from *Arabidopsis*: isolation and in vitro reconstitution. *Proc Natl Acad Sci USA* 96, 7110-7115

Clemens, S. et al., (1999) Tolerance to toxic metals by a gene family of phytochelatin synthases from plants and yeast. *EMBO J.* 18, 3325-3333

Chen, J. et al. (1997) Characterization of phytochelatin synthase from tomato. *Physiol. Plant.* 101, 165-172

Zenk, M. H. (1996) Heavy metal detoxification in higher plants—a review. *Gene*, 179, 21-30

Gisbert, C. et al. (2003). A plant genetically modified that accumulates Pb is specially promising for phytoremediation. *Biochem. Biophys. Res. Commun.* 303, 440-445

Salt, D. E. and Rauser, W. E. (1995) MgATP-dependent transport of phytochelatins across the tonoplast of oat roots. *Plant Physiol* 107, 1293-1301

Salt D. E., Wagner G. J. (1993) Transport of Cd in tonoplast vesicles from oat roots. Evidence for a Cd/H antiport activity. *J Biol Chem* 268, 12297-12302

Cobbett, C. S. (2000) Phytochelatins and their roles in heavy metal detoxification. *Plant Physiol.* 123, 825-832

Takagi, M. et al. (2003) Cellular Toxicity of Cadmium Ions and Their Detoxification by Heavy Metal-Specific Plant Peptides, Phytochelatins, Expressed in Mammalian Cells. *J. Biochem.* 131, 233-239.

DETAILED DESCRIPTION

Figure 1:
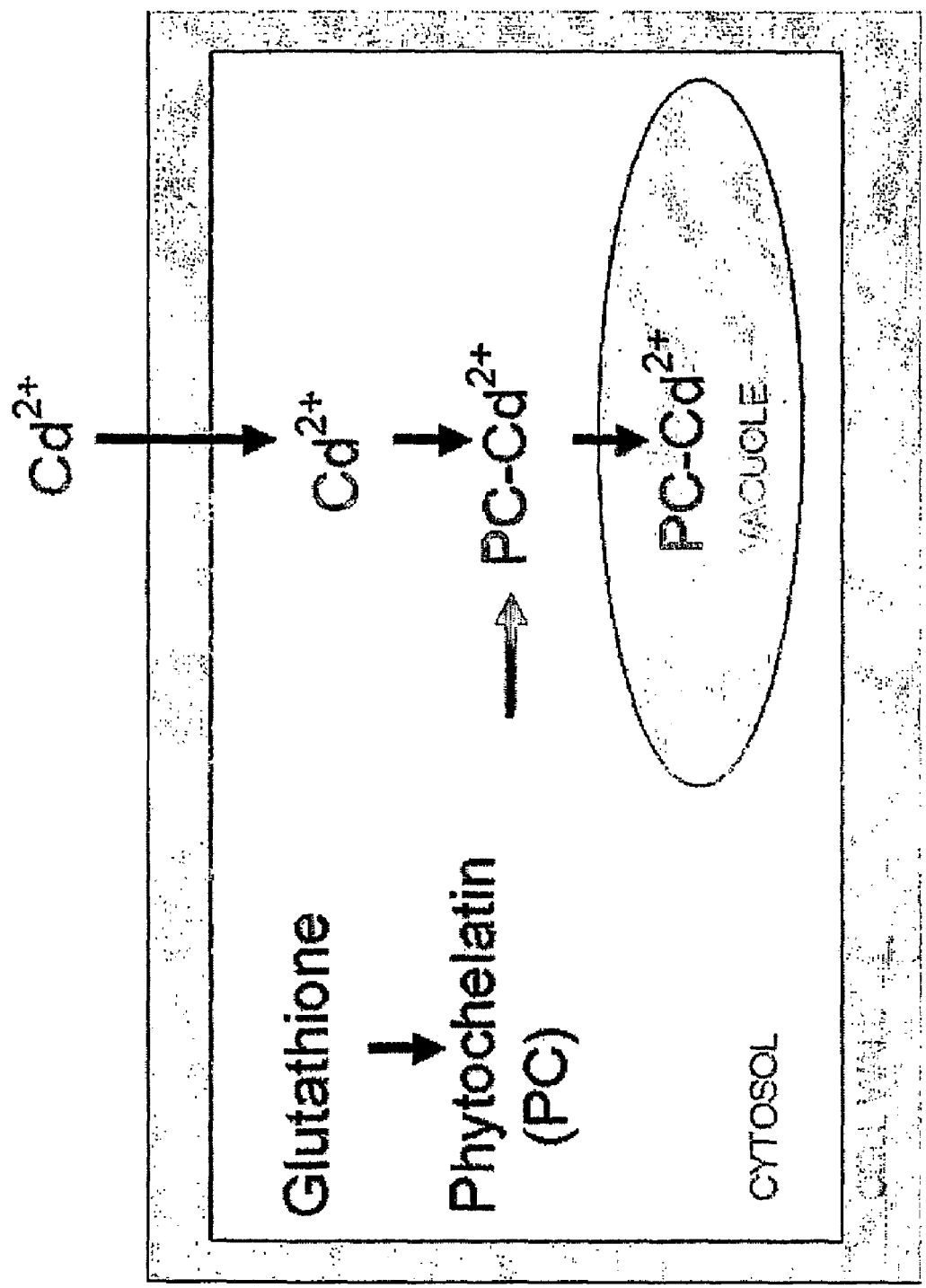
FIG. 1. is a chart showing PC biosynthesis in plants and yeast. Glutathione (GSH) is a substrate for phytochelatin synthase (PCS). Cd is a positive effector of γ-ECS, Glutathione synthase (GS) and PCS. γ-ECS is also feedback regulated by GSH. Both γ-ECS and CS are ATP dependent. Cd is a positive effector of CS. The phytochelatin is bound to Cd and forms a complex PC-Cd. The complex is transported inside the vacuole by a transporter type YCF1.

The binary Ti vector pBI121 (Clontech) was used for transformation. The GUS gene of the binary vector was replaced with the wheat phytochelatin synthase 1 cDNA (TaPCS1, Accession No. AF093752) to gain the new construct pBI-TaPCS1. The TaPCS1 cDNA (donation of Professor Julian Schroeder, University of California, San Diego) was originally cloned in pYES2 (Invitrogen) and designated pYESTaPCS1. The plasmid was digested with XhoI and converted to blunt ends with the DNA polymerase I (Klenow fragment). Afterwards, pYESTaPCS1 was digested with BamHI to produce a 2-kb insert containing the TaPCS1 cDNA. PBI121 was digested with BamHI and ECL136II. The 2-kb TaPCS1 insert was ligated to the BamHI-Ecl136II sites of plasmid pBI121. The new construct (pBITaPCS1) was electroporated into *Agrobacterium tumefaciens* strain C58C1RifR Rif (Van Larebeke et al. 1974).

*Nicotiana glauca* leaf explants were infected with *A. tumefaciens* after two days of preculture on organogenic medium NB2510 [MS salts (Murashige y Skoog, 1962) including Gamborg B5 vitamins (DUCHEFA), 3% sucrose, 2.5 µg mL$^{-1}$ naphthalene acetic acid (NAA), 1 µg mL$^{-1}$ of 6 benzyl aminopurine (BA), and 0.8% agar (bacteriologic agar "Europeo" PRONADISA) in the dark. Explants from adult and young leaves were infected by immersion on *Agrobacterium* culture for 10 min. After 1 day of cocultivation, explants were transferred to selection medium NB2510 containing 100 µg mL$^{-1}$ kanamycin and 350 µg mL$^{-1}$ carbenicillin. Two months after infection, shoots were individually removed from the call using explants and transferred to bottles containing 30 ml of B1 medium (MS salts including Gamborg B5 vitamins, 0.3 µg mL$^{-1}$ indol acetic acid or 0.2 µg mL$^{-1}$ NAA, 1% sucrose, 100 µg mL$^{-1}$, and 0.7% plant agar).

The invention claimed is:

1. A plant species transformed for the phytoremediation of a soil contaminated with heavy metals, the plant species comprising: a progenitor plant of *Nicotiana glauca* genetically transformed with the gene TaPCS1, wherein the progenitor plant of *Nicotiana glauca* is obtained from polluted soils.

2. The plant species according to claim 1, wherein the heavy metals are selected from the group consisting of cadmium, lithium, arsenic, copper, chromium, silver, zinc, lead, mercury, nickel, cobalt, tin, ruthenium, rhodium, uranium, iridium, polonium uranium, cesium, boron, osmium, niobium, tantalum, gold, antimony, bismuth, indium, scandium, titanium, palladium, zirconium, platinum, technetium, rhenium, lantanids and actinids.

3. The plant species according to claim 1, wherein the TaPCS gene is in a binary Ti vector pBI121.

4. The plant species according to claim 1, wherein the plant is a wild type plant and is being used for the same soil or for other polluted soil after creation of the genetically transformed plant.

5. The plant species according to claim 2, wherein the heavy metals in the soil are selected from the group consisting of cadmium and lead.

6. A plant species transformed for the phytoremediation of a soil contaminated with heavy metals; the plant species comprising: a progenitor plant of *Nicotiana glauca* genetically transformed with the gene TaPCS1, wherein the progenitor plant of *Nicotiana glauca* is obtained from polluted soils, and wherein the contaminated soil comprises at least 1,500 ppm of lead and/or at least 2,500 ppm of zinc.

7. A method for phytoremediating a soil contaminated with heavy metals, the method comprising the steps of:
    1) obtaining a progenitor *Nicotiana glauca* plant from a polluted soil;
    2) transforming the *Nicotiana glauca* plant with the gene TaPCS1; and
    3) transferring the transformed *Nicotiana glauca* plant to the contaminated soil.

8. The method of claim 7, wherein the contaminated soil comprises at least 1,500 ppm of lead and/or at least 2,500 ppm of zinc.

* * * * *

SEQUENCE LISTING

<160> NUMBER OF SEQ ID NOS: 27

<210> SEQ ID NO 1
<211> LENGTH: 1044
<212> TYPE: DNA
<213> ORGANISM: Arabidopsis thaliana

<400> SEQUENCE: 1

```
atggcttcaa attcagcact tctcatgaaa acaatcttcc tcgtactcat tttttgtctct      60 tttgcaatct ctccagcaac ttcaactgcg ccggaagaat gtggaagcga gtcagcgaac      120
ccgtgcgtca acaaagctaa agctttgcct ctcaaagtca tagcaatctt cgtaatcctc      180
```

-continued

```
attgcaagca tgattggtgt tggagctcct ctctttagcc gtaacgtttc gttcctccaa    240
ccagacggaa acatcttcac tatcattaag tgtttcgcct ccgggatcat ccttggaacc    300
ggttttatgc acgttttacc tgattctttc gaaatgttgt catctatatg tcttgaagag    360
aacccgtggc ataaatttcc tttctccgga tttctcgcta tgttatcggg tctaatcact    420
ctagccattg actccatggc cacgagccta tacaccagca agaacgcagt tggtatcatg    480
ccccatggtc atggtcatgg tcacggcccc gcaaatgatg ttaccttacc aataaaagaa    540
gatgattcgt caaatgcaca gctcttgcga taccgagtca ttgccatggt cttggaactt    600
gggatcatag ttcactcggt ggtcattgga ttatctctag gagcaactag tgacacttgc    660
accattaaag gacttatagc agctctttgc ttccatcaaa tgttcgaagg catgggtctt    720
ggcggttgta tcctccaggc tgagtataca aatatgaaga aatttgttat ggcgttcttt    780
ttcgcggtaa caacaccatt cggaatagcg ttagggatcg ctctatcaac tgtttaccaa    840
gataatagcc caaaagcttt gatcacggtt ggacttctaa atgcatgctc cgctggattg    900
ctcatttaca tggcactcgt ggatcttcta gctgcggagt tcatgggacc taagcttcaa    960
ggtagcatca aaatgcagtt caagtgttta atcgcggctc ttctcgggtg cggtggaatg    1020
tcgattatcg ccaaatgggc ttaa    1044
```

<210> SEQ ID NO 2
<211> LENGTH: 1053
<212> TYPE: DNA
<213> ORGANISM: Arabidopsis thaliana

<400> SEQUENCE: 2

```
atggctacta ccaagctcgt ctacattctc ctcatcctat tcaccttcac cgtatctccg    60
gcgatctcaa cggccccgga acattgtgat agcggctttg ataacccgtg catcaacaaa    120
gctaaggctt taccactcaa aatcgtagcc attgttgcca tacttacaac aagcttgata    180
ggcgtgacct ctcctctttt cagccgttac atttcgttcc tcgtcccga tggcaatggt    240 ttcatgatcg tcaaatgttt ttcttctgga atcatccttg gaaccggttt catgcacgtc    300
ttgcctgact ctttcgagat gttgtcatcg aaatgtctta gtgataatcc gtggcataag    360
ttcccttttg cgggttttgt cgctatgatg tccggtctag tcactctagc cattgactcc    420
attaccacca gcctttatac cggtaagaac tcagtcggac cagtgcctga tgaagagtat    480
ggcattgatc aagagaaagc gattcacatg gtaggccaca atcatagtca cggtcatggt    540
gtagtgctag caactaaaga tgatggacag cttttgcgct accaagtcat tgccatggta    600
ttggaggttg gcatttttatt tcattctgtg gtcattggac tatctctagg agcaactaat    660
gattcatgta ccattaaagg actcatcata gctctttgct tccatcactt gttcgaaggc    720
ataggtcttg gtggctgcat cctccaggca gattttacaa atgtgaagaa gttcttgatg    780
gcattctttt tcactggaac aacaccttgt ggtatctttc ttggaatcgc attgtcgagt    840
atctatagag ataacagtcc aaccgcgttg attacgattg gactgttaaa tgcttgctcg    900
gccggaatgc tcatctacat ggccctcgtc gaccttctag ctaccgagtt catggggtca    960
atgctccaag gtagcatcaa acttcagatc aagtgcttca cggcggcttt gcttggctgc    1020
gccgtaatgt cggtcgtcgc cgtgtgggct taa    1053
```

<210> SEQ ID NO 3
<211> LENGTH: 1068
<212> TYPE: DNA

<213> ORGANISM: Arabidopsis thaliana

<400> SEQUENCE: 3

| | | | | | |
|---|---|---|---|---|---|
| atgtctgaat | gtggatgttt | ttcggcaaca | actatgttga | gaatttgtgt | agtattgata | 60 |
| atatgtttgc | atatgtgttg | tgcctcgagt | gattgtacaa | gtcacgatga | tcctgtgtct | 120 |
| caagacgaag | cagagaaagc | gacgaagcta | aagcttggtt | cgatagcttt | acttcttgta | 180 |
| gccggaggag | tcggcgtgag | tctaccgttg | atcgggaaaa | ggattccggc | gttacaaccg | 240 |
| gaaaatgata | tcttcttcat | ggtgaaagct | tttgctgcag | gagtgatcct | ctgcacaggt | 300 |
| ttcgttcata | tcttaccaga | cgcgttcgag | agattgagct | ctccatgtct | tgaggacact | 360 |
| acagctggga | agttcccgtt | tgctggtttt | gtagcgatgc | tgtcggcgat | ggggactctt | 420 |
| atgatcgaca | cattcgcgac | agggtattac | aagaggcaac | attttagcaa | taaccatggg | 480 |
| agcaagcaag | tgaacgtagt | agtagatgaa | gaagagcatg | cgggtcatgt | tcacattcac | 540 |
| acgcacgcta | gtcacggaca | cacacatggt | tcgaccgagt | tgatcagaag | acgtatagtg | 600 |
| tcgcaggtgc | ttgagattgg | gatagttgtg | cattcggtta | ttatagggat | atcacttgga | 660 |
| gcttcacaga | gcatagacac | cataaagcca | ctcatggctg | cactatcttt | ccatcagttc | 720 |
| tttgaaggtc | ttggcctcgg | tggatgcatc | tccctggcgg | atatgaagtc | gaaatcgaca | 780 |
| gtgctaatgg | cgacattttt | tcggtgacg | gcgccacttg | gataggaat | agggttgggg | 840 |
| atgtcaagtg | gtttaggcta | caggaaagag | agcaaagagg | caataatggt | ggaaggaatg | 900 |
| ttgaatgctg | catctgctgg | gatactcata | tacatgtcac | ttgttgatct | tcttgctact | 960 |
| gattttatga | atccaagatt | gcaatccaat | ctctggcttc | acttggctgc | ttatctctct | 1020 |
| ctcgtcctag | gcgcaggttc | catgtctctc | ctcgccatct | gggcctga | | 1068 |

<210> SEQ ID NO 4
<211> LENGTH: 1062
<212> TYPE: DNA
<213> ORGANISM: Arabidopsis thaliana

<400> SEQUENCE: 4

| | | | | | |
|---|---|---|---|---|---|
| atggctttgt | cttccaaaac | cctaaagtca | actctcgtct | tcctctctat | tattttcctc | 60 |
| tgtttctcct | tgatcctagc | tcacggcggc | atagacgacg | gcgacgaaga | agaggagacc | 120 |
| aaccagccac | ctccggccac | cggaacaacc | accgtcgtga | atctccgatc | caaaggcttg | 180 |
| gtgcttgtga | agatctactg | tattataata | ctcttcttta | gcacattctt | agccggaatt | 240 |
| tcaccttact | tttaccgatg | gaacgagtcg | tttctcctcc | taggaactca | attctccggt | 300 |
| ggtatattcc | tcgcgaccgc | tctaatccat | ttcctcagcg | acgctaacga | gactttccga | 360 |
| gggttaaaac | acaaagagta | tccttacgct | ttcatgttag | cagccgctgg | atattgcctt | 420 |
| acaatgctgg | cagatgtggc | ggttgcgttt | gtagcggctg | ggagtaataa | caaccacgtc | 480 |
| ggagctagcg | tcgagagtc | gagggaggat | gatgacgtgg | cagtgaaaga | ggaaggacgt | 540 |
| cgtgagataa | agagtggtgt | tgatgtgagt | caagcgctta | tacgaactag | tggatttgga | 600 |
| gacacagctt | tgctgatttt | tgctctttgt | tttcactcca | tctttgaggg | aatcgccatt | 660 |
| ggtctctcag | acactaaaag | cgacgcttgg | agaaacctat | ggacaatatc | gttgcacaag | 720 |
| gtctttgcgg | ccgtagcaat | gggaatagct | cttctcaagc | taatccctaa | acgtccattc | 780 |
| ttcctcactg | tcgtctactc | cttcgccttt | gggatatcga | gtcccatagg | tgtcgggatt | 840 |
| ggcattggaa | tcaatgccac | tagccaagga | gctggtggtg | actggaccta | cgcgatctct | 900 |
| atggggcttg | cgtgtggagt | ttttgtgtac | gttgcggtta | accatctcat | ctcaaaaggg | 960 |

```
tataagcctc ttgaggaatg ttacttcgac aagccaatct acaagtttat tgccgtcttc   1020
ctcggtgttg ctttgctctc tgttgtaatg atttgggatt ga                      1062

<210> SEQ ID NO 5
<211> LENGTH: 1020
<212> TYPE: DNA
<213> ORGANISM: Arabidopsis thaliana

<400> SEQUENCE: 5
atgaagacta agagcgtgaa actcttattc ttcttcttct ccgtctccct ccttctcatc     60
gccgtcgtca acgccgccga aggccattca catggtggac aaaatgtga atgctcacac    120 gaagacgacc atgaaaacaa agccggagct cggaaataca agatcgccgc aattcctaca   180
gttctaatag ccggcataat cggagttctt ttccctttgt taggcaaagt cttcccttct   240
ttgcgtccag aaacatgttt cttcttcgtc acgaaagctt tcgcagccgg agttatcttg   300
gctaccggat ttatgcatgt cttgcctgag gcttacgaga tgcttaactc tccatgtttg   360
atatctgaag catgggaatt ccgttcacc ggatttattg cgatgattgc tgcgatcttg    420
acgttatccg ttgatacatt tgccacttcg agtttctata atcgcattg caaagcgtct    480 aagagggtca gtgatggaga aaccggcgag tcctccgttg actccgagaa ggtccaaatt   540
ctccggacta gagttattgc acaggtattg gagttggaa taatagtaca ctcagtggta    600
ataggaatat cactaggagc ttcacagagc ccagatgctg caaaagctct gtttattgcc   660
ttaatgtttc atcaatgctt cgaaggtcta ggccttggtg gttgtattgc tcagggaaaa   720
ttcaagtgtt tgtcagtaac aatcatgtcg acgttcttcg caataacgac accgatagga   780
atcgttgtgg gaatgggaat agcaaattct tacgatgagt cttcaccaac ggctctgatc   840
gttcaaggag ttttgaacgc tgcatccgca ggcattctca tctacatgtc tttggttgac   900
cttctcgcag cagatttcac gcaccctaaa atgcaatcca atactgggct tcaaattatg   960
gcccatattg ctctccttct tggtgctggc tcatgtctc tattggctaa atgggcttga    1020

<210> SEQ ID NO 6
<211> LENGTH: 1131
<212> TYPE: DNA
<213> ORGANISM: Saccharomyces cerevisiae

<400> SEQUENCE: 6
atgagcaacg ttactacgcc gtggtggaaa caatgggacc cttctgaagt tacacttgcc    60
gataaaaccc ctgatgatgt gtggaagacc tgtgttttgc aaggtgttta ctttggtgga   120
aacgagtaca atggtaactt aggtgccaga atatcttccg tctttgttat tcttttcgtg   180 agtactttt tcaccatgtt cccattaatc tcaacaaaag tgaaaagatt gagaattcct    240
ctatatgttt accttttcgc aaagtatttt ggttccggtg ttattgttgc aaccgcattt   300
atccacttaa tggaccctgc ttatggtgcg attggtggta ccacttgtgt aggacaaacc   360
ggtaactggg tctttattc atggtgtcct gccattatgc taacgagttt gaccttcact   420
ttccttactg atctattcag tagcgtctgg gttgaaagaa gtatggtct ttcccatgac    480 catacccacg atgaaattaa agacactgtt gtgagaaaca ctgcagctgt tcaagtgag   540 aatgacaatg agaatggtac tgcaaatgga tctcatgaca ccaagaacgg agtagagtat   600
tatgaagatt cagacgctac atccatggat gttgttcaat catttcaagc acaatttat    660 gccttttaa ttttagaatt cggtgtgatt ttccactccg ttatgatcgg tctaaacctg    720
```

| | |
|---|---:|
| ggaagtgttg gtgatgagtt ctcctcccta taccctgtct tagtgttcca tcaatcattt | 780 |
| gaaggtttag gtattggtgc aagattgtca gccattgaat tccctagatc aaagagatgg | 840 |
| tggccatggg ccctatgtgt tgcgtatggg ttaaccacac caatctgtgt ggccatcggt | 900 |
| ttgggtgttc gtaccagata cgtcagcggt tcttacactg cgcttgttat ctctggtgtt | 960 |
| ttggatgcca tttctgctgg tatcttattg tacactggtt tggttgaact actagcaaga | 1020 |
| gactttatat tcaatcctca aagaacaaag gatctaagag aattgtcctt caacgttata | 1080 |
| tgcactcttt tcggtgctgg tatcatggct ttgatcggta agtgggctta a | 1131 |

<210> SEQ ID NO 7
<211> LENGTH: 1269
<212> TYPE: DNA
<213> ORGANISM: Saccharomyces cerevisiae

<400> SEQUENCE: 7

| | |
|---|---:|
| atggttgatc ttatagcgag ggatgactcc gtagatactt gccaagcttc taacggctac | 60 |
| aatgggcacg caggtcttag aattctggca gtattcatta tactgatatc gtcaggattg | 120 |
| ggagtttatt tcccaatttt gtcatcacgg tattcgttta taaggctacc aaattggtgc | 180 |
| tttttcatag cgaagttctt cggttctggt gtcattgttg ccacagcgtt cgttcatctt | 240 |
| ctacagcccg cagccgaagc tctgggagat gaatgtcttg gtggcacatt tgccgaatat | 300 |
| ccatgggctt ttgggatctg tttaatgtcg cttttcttac ttttcttcac tgaaatcatc | 360 |
| acgcattatt ttgtagcgaa aacgctggga cacgatcatg gggaccatgg ggaagttacc | 420 |
| agtattgatg ttgatgctcc cagttcggga tttgtcatca gaaatatgga ctcggatcct | 480 |
| gtatctttca ataacgaagc tgcctactcc atccataatg acaaaactcc gtacactact | 540 |
| agaaatgaag agattgtcgc tactcctata aaggaaaaag aacccggctc aaatgttact | 600 |
| aattatgatc tggaaccggg aaaaacagag tcactagcta atgaactagt tccaaccagt | 660 |
| tcccatgcga caaatctcgc ttctgtacct ggaaaagatc attattctca cgaaaatgac | 720 |
| catcaagatg tctcccagtt ggccacacgt atcgaggagg aagataaaga gcagtatctc | 780 |
| aatcagatac tagctgtttt tattctagaa tttggcatca tctttcactc tgtatttgtg | 840 |
| ggtctttcgc tatctgtcgc gggtgaagaa ttcgaaacct tatttatcgt tttaactttc | 900 |
| caccaaatgt tcgaaggttt gggtctaggc acaagagttg ccgaaacgaa ttggccagaa | 960 |
| agtaagaagt acatgccttg gttaatggga ttagccttca ctttaacgtc acccatagca | 1020 |
| gtcgcggtag gtattggtgt cagacactct tggatacctg gctctagaag agcattaatt | 1080 |
| gctaatggtg ttttttgactc gatatcatca ggaattctta tttatactgg actagtcgaa | 1140 |
| ttaatggctc atgaattctt atactctaat caattcaaag gacctgatgg cctcaaaaaa | 1200 |
| atgcttagtg catatctcat catgtgttgt ggagctgctt taatggctct tctagggaaa | 1260 |
| tgggcatag | 1269 |

<210> SEQ ID NO 8
<211> LENGTH: 948
<212> TYPE: DNA
<213> ORGANISM: Arabidopsis thaliana

<400> SEQUENCE: 8

| | |
|---|---:|
| atggctacga ctactcaaca catgaatcaa atcttcctcg tactcctcct aatctccttc | 60 |
| gcaatctctc cggcgatctc aacggttcca aagaatgcg agaccgattc aacagactct | 120 |
| tgcatcgata aaaccaaagc cttacctctc aaaattgtag caatcgttgc catcctcgtg | 180 |

| | |
|---|---|
| acaagcatga tcggagtcgc agctcctctc tttagccgat atgtcacatt cctgcatcca | 240 |
| gatggtaaaa tctttatgat cattaagtgt tttgcatccg ggatcatcct aggaaccggc | 300 |
| ttcatgcatg ttttgcccga ttctttcgag atgttgtcct ctccatgtct tgaagacaat | 360 |
| ccatggcaca agtttccctt cactggcttt gtcgctatgt tgtccggtct tgtaactctt | 420 |
| gctattgact ctatcgctac aagtctctac accaagaaag ctgtcgctga tgacagcgaa | 480 |
| gaaaggacta ctcctatgat aattcaaatc gatcatttgc ctctaacaac taaagaacgt | 540 |
| agctctacat gctcaaaaca actattgcgg taccgagtta tcgccacggt cttggagctt | 600 |
| gggataatag ttcactccgt ggtcattgga ctatctctag gtgcaaccaa cgacacatgc | 660 |
| actattaaag gccttattgc agctctttgc ttccatcaaa tgttcgaagg gatgggtctc | 720 |
| ggcgccttgt cgagcgttta caaagacaac agtccaacag cattaatcac ggtaggactg | 780 |
| ctcaatgctt gttctgcagg attgctcatt tatatggcac ttgtagatct tctagccgca | 840 |
| gagtttatgg gatctatgct ccaaagaagc gtcaagcttc agcttaactg cttcggggca | 900 |
| gctttgcttg ggtgtggcgg aatgtcagtc ctggccaagt gggcataa | 948 |

<210> SEQ ID NO 9
<211> LENGTH: 1428
<212> TYPE: DNA
<213> ORGANISM: Arabidopsis thaliana

<400> SEQUENCE: 9

| | |
|---|---|
| atggcgggaa tcgtgacaga gccgtggtca gtagctgaga acggaaaccc aagcataacg | 60 |
| gcgaaaggat cgagcagaga actaagactt ggaagaaccg ctcacaacat gtcttcttct | 120 |
| tctttgagga aaaaatcaga cctccgagtg attcagaagg ttccatacaa aggtcttaaa | 180 |
| gattttctct ctaatctcca agaagtcatt ctcggaacaa agcttgccat tcttttccg | 240 |
| gccattcctg ccgccattat ttgcacctat tgtggcgtca gtcagccttg atatttggaa | 300 |
| cttagcttgc taggactgac acctttggct gagcgagtca gcttttgac agagcaacta | 360 |
| gctttctaca ccggtcctac attgggtggt ctattgaacg caacgtgtgg aaacgcgact | 420 |
| gaattgataa tcgcgattct tgcttttgacc aataacaaag tcgcagtggt gaaatattcg | 480 |
| ctgctaggtt cgattttgtc gaaccttta ttggttctag ggacttcact cttctgtgga | 540 |
| ggaatcgcta atatccgaag ggaacagcgg ttcgaccgga acaagccga tgtgaacttc | 600 |
| ttcttacttc tactgggttt cttgtgtcac ttgctgccat tgttggtggg atacttgaaa | 660 |
| aacggagagg cttcggctgc tgttttgtcc gacatgcaac tgagtatatc gcgaggcttc | 720 |
| agtattgtta tgttgatcag ctacattgca tatcttgttt tccaactgtg gactcaccgc | 780 |
| caattgttcg atgcacaaga acaggaagat gagtatgatg acgatgtgga gcaagaaacc | 840 |
| gcggtgatta gttttggag cggttttgca tggttggttg ggatgacact cgttatcgca | 900 |
| ttgctatcgg agtatgttgt agccacgatt gaggaagcat cggataaatg gaacttatca | 960 |
| gtgagtttca taagcatcat attgcttcct attgttggaa atgcagctga acatgctgga | 1020 |
| gccgttattt ttgcctttaa gaacaagctt gacatatctt tgggagttgc gttaggctct | 1080 |
| gcgactcaga ttggcttatt cgttgtcccc ttgaccatca tcgtggcgtg gattttggga | 1140 |
| attaatatgg atctcaattt tggtcccctc gaaactggct gtcttgctgt ttccataatc | 1200 |
| atcacagcgt tcacattaca ggatgggagt tctcactaca tgaagggact ggtcctcttg | 1260 |
| cttttgctatt tcattattgc catctgtttc ttcgtcgaca aacttcccca gagtgagtta | 1320 |

| gttttcaaat gtatatgcat gctattatta gggaaaacaa taattgaggc atacaacacc | 1380 |
| catatatcaa atggaaatgc ttcatcaaat aaagttaaaa cgggttaa | 1428 |

<210> SEQ ID NO 10
<211> LENGTH: 1380
<212> TYPE: DNA
<213> ORGANISM: Arabidopsis thaliana

<400> SEQUENCE: 10

| atgggaagta tcgtggagcc atgggcagca atcgccgaga acggaaacgc aaacgtgacc | 60 |
| gcgaaaggct cgagcaggga gctgcgcat gggagaacag cacacaacat gtcttcatcg | 120 |
| tcgctaagga agaaatcaga cctgagattg gttcagaaag ttccatgcaa aactctcaag | 180 |
| aacattctct ctaatcttca agaagtcatt cttggtacta agcttactct cttatttctc | 240 |
| gccatccctc tcgccattct tgccaattct tacaactacg gtcgtccgtt gatatttgga | 300 |
| ctgagcttga taggactgac acctctagct gagcgagtta gcttttgac agagcaacta | 360 |
| gctttctaca ctggtccaac agtgggcggt tgttgaacg cgacttgtgg aaacgcgaca | 420 |
| gagctgataa tcgcgatact agcgttggcc aataacaaag tggcagtggt gaaatactct | 480 |
| ctattgggtt caattctctc aaaccttctc ttggttcttg cacttccct cttctttggt | 540 |
| ggtatcgcca atatccgccg cgagcagcgg ttcgaccgga acaagccga tgtgaacttc | 600 |
| ttcttgctgc ttatgggcct gttgtgtcat tgctgccat tattgttaaa atatgcagca | 660 |
| accggcgaag tatcgacctc tatgattaac aaaatgtcgc tcactctgtc gcggacaagc | 720 |
| agcatagtta tgcttattgc ttacattgct tatctcatct tccagctctg gactcaccgc | 780 |
| caattgtttg aggcacaaca ggatgatgat gatgcatatg atgatgaggt tagtgttgaa | 840 |
| gaaactccag tgataggatt ctggagcgga tttgcttggc tcgttgggat gacaatagtc | 900 |
| atcgcattgc tatcagagta tgttgtggac acgatcgagg atgcatcgga ctcatgggga | 960 |
| ctatcagtga gtttcataag catcatattg cttcccattg ttgggaatgc ggctgagcat | 1020 |
| gctggagcca tcattttcgc attcaagaac aagctcgaca tatctctagg ggttgcgttg | 1080 |
| ggctctgcaa ctcagatttc tttgttcgtg gtcccattga gtgttatcgt tgcgtggatc | 1140 |
| ctgggaataa aaatggatct caactttaac atccttgaaa ctagctctct agctttggcc | 1200 |
| attatcatca cagccttcac tttacaggat ggaacttctc attacatgaa gggactggtt | 1260 |
| ctattgttat gctatgtcat catcgcggcg tgtttcttcg tcgaccaaat tccccaacca | 1320 |
| aatgatttgg acgtgggact tcaacccatg aacaatttgg gagaagtttt ctcagcttaa | 1380 |

<210> SEQ ID NO 11
<211> LENGTH: 1530
<212> TYPE: DNA
<213> ORGANISM: Arabidopsis thaliana

<400> SEQUENCE: 11

| atgccacaac tcgagaacaa cgagccactt ctaatcaacg aggaagaaga agaagaaaca | 60 |
| gcgtacgatg aaacagagaa ggtacatatc gtaagaaacg aagaggagga cgatctagaa | 120 |
| cacggcgtcg gatgcggcgg cgcaccaccg ttctcatgga agaagctatg gttattcacc | 180 |
| ggacctgggt ttttaatgag cattgcgttt ttagatccag gaatctcga aggagatctt | 240 |
| caagccggtg cggttgctgg gtactctttg ttatggcttc tcatgtgggc aacagcaatg | 300 |
| ggtcttttgg ttcagctttt gtcggctagg cttggtgttg cgacaggtcg tcacttagct | 360 |
| gagctttgtc gtgatgagta tcctacttgg gcaagaatgg ttttgtgggt tatggctgaa | 420 |

-continued

| | |
|---|---|
| ttggctttga ttggatctga tattcaagaa gttattggta gtgctattgc tatcaagatt | 480 |
| ttgagtaatg ggattttgcc tctttgggct ggtgttgtta ttactgctct tgattgtttc | 540 |
| gtcttcttgt ttcttgagaa ctacggaata aggaagctcg aggctgtgtt tgcagttctt | 600 |
| atcgctacaa tgggagtctc attcgcttgg atgtttggtc aagctaagcc aagtggctct | 660 |
| gagcttctca ttgggatttt ggtaccgaaa ctgagttcaa gaacgataca gaaagcagtt | 720 |
| ggagttgtgg gttgcattat aatgccacac aatgtgtttc ttcactcagc tcttgttcaa | 780 |
| tctagagaag tcgataaacg acagaaatac cgagtccaag aagcgctaaa ctactacaca | 840 |
| atagaatcca caattgctct tttcatctcc tttttgatca atctgtttgt cacaactgtt | 900 |
| ttcgccaaag ggttttataa tactgacctc gccaatagca tcggtttggt taacgcggga | 960 |
| cagtatcttc aggagaaata tggaggcggt gtgttcccga tactatacat ttgggcgatc | 1020 |
| gggctattag ctgctggcca aagcagcact attaccggta catatgcggg acagttcata | 1080 |
| atgggcgggt tcttaatttt caaaatgaag aaatggttga gagctttgat cacacgaagc | 1140 |
| tgcgctatca ttccaactat tatcgttgcg ctagtgtttg attcatcgga agctacactc | 1200 |
| gatgtcttaa cgagtggct taacgtgctt cagtccattc aaatccccctt tgcactcatt | 1260 |
| cccttacttt gtttggtctc caaggaacaa atcatgggta gcttcaagat tggtcctttg | 1320 |
| tacaagacaa tcgcgtggct tgttgctgcg ctcgtgataa tgatcaacgg ttatcttttg | 1380 |
| ttggagttct tctccaatga ggttagtggc atagtctata ccggttttgt gacactgttc | 1440 |
| acagcttctt atggtgcatt catcctctac ctcattgctc gtggcatcac tttcactcct | 1500 |
| tggccgttca aagcggagtc tagtcattga | 1530 |

<210> SEQ ID NO 12
<211> LENGTH: 1044
<212> TYPE: DNA
<213> ORGANISM: Arabidopsis thaliana

<400> SEQUENCE: 12

| | |
|---|---|
| atggctacga ctactcaaca catgaatcaa atcttcctcg tactcctcct aatctccttc | 60 |
| gcaatctctc cggcgatctc aacggttcca aaagaatgcg agaccgattc aacagactct | 120 |
| tgcatcgata aaccaaagc cttacctctc aaaattgtag caatcgttgc catcctcgtg | 180 |
| acaagcatga tcggagtcgc agctcctctc tttagccgat atgtcacatt cctgcatcca | 240 |
| gatggtaaaa tctttatgat cattaagtgt tttgcatccg ggatcatcct aggaaccggc | 300 |
| ttcatgcatg ttttgcccga ttcttcgag atgttgtcct ctccatgtct tgaagacaat | 360 |
| ccatggcaca gtttcccctt cactggcttt gtcgctatgt tgtccggtct tgtaactctt | 420 |
| gctattgact ctatcgctac aagtctctac accaagaaag ctgtcgctga tgacagcgaa | 480 |
| gaaaggacta ctcctatgat aattcaaatc gatcatttgc ctctaacaac taagaacgt | 540 |
| agctctacat gctcaaaaca actattgcgg taccgagtta tcgccacggt cttggagctt | 600 |
| gggataatag ttcactccgt ggtcattgga ctatctctag gtgcaaccaa cgacacatgc | 660 |
| actattaaag gccttattgc agctctttgc ttccatcaaa tgttcgaagg gatgggtctc | 720 |
| ggcggttgca tccttcaggc agaatataca aatgtgaaga aatttgtgat ggccttcttc | 780 |
| tttgctgtta caacaccatc aggaatcgct cttggtatag ccttgtcgag cgtttacaaa | 840 |
| gacaacagtc caacagcatt aatcacggta ggactgctca atgcttgttc tgcaggattg | 900 |
| ctcatttata tggcacttgt agatcttcta gccgcagagt ttatgggatc tatgctccaa | 960 |

```
agaagcgtca agcttcagct taactgcttc ggggcagctt tgcttgggtg tggcggaatg    1020
tcagtcctgg ccaagtgggc ataa                                           1044

<210> SEQ ID NO 13
<211> LENGTH: 1095
<212> TYPE: DNA
<213> ORGANISM: Arabidopsis thaliana

<400> SEQUENCE: 13
atgactaaat ctcatgtcat tttctctgcc tccatcgctc tctttctcct actctccatc      60
tcgcatttcc cgggagctct ctctcaatcc aataaagatt gccaatcaaa atccaactac     120
tcatgtatag acaaaaacaa agcattagat ctcaaactct tatcaatctt ctcaattctc     180
atcactagtc taatcggtgt ttgcctcccg ttctttgccc gatcaattcc cgcttttcaa     240
cccgagaaat ctcacttcct catcgtaaaa tctttcgcct ccggaatcat cctttccact     300
ggtttcatgc atgtcttgcc tgattctttc gagatgcttt catctccttg tcttaacgat     360 aaccctggc acaagtttcc tttcgccggc tttgtagcca tgatgtctgc cgtgttcacg      420
ctcatggttg actctattac caccagcgtc ttcaccaagt caggaaggaa agatctacgt     480
gctgacgtag catccgttga gactcctgac caagagatag ggcacgtaca ggttcatggc     540
catgttcata gccatactct tcctcacaat cttcatggag agaatgataa agagcttggt     600
tcttatttac agcttctgcg gtatcgtatt cttgcaatcg tattggagct aggaatagtg     660
gtgcagtcga tagtgatagg actatcggta ggagacacta acaatacttg caccatcaaa     720
ggactcgtcg ctgcgctttg cttccatcaa atgttcgaag gcatgggtct cggcggttgc     780
atccttcagg cggagtacgg gtgggttaaa aaggcggtga tggctttctt ttttgcggtg     840
acgacgcctt ttggagtggt tctagggatg gcactatcta aaacatacaa agagaatagc     900
cctgaatcgc ttataacagt tgggttgctc aacgcttcct cggcaggact actcatctac     960
atggctttag ttgaccttct agctgccgat tttatgggtc aaaaaatgca aaggagcatc    1020
aagcttcaat taaagtcata tgctgccgtt ttgcttggtg ctggtggcat gtccgtcatg    1080
gccaagtggg cttga                                                     1095

<210> SEQ ID NO 14
<211> LENGTH: 1401
<212> TYPE: DNA
<213> ORGANISM: Capsela bursa-pastoris

<400> SEQUENCE: 14
atggctggaa tcgtaacaga accgtgggca tcggcggaga acggaaacgc aagcatgaca      60
gcgaaaggat cgagcagaga actgagacat ggaagaacag ctcacaacat gtcatcttct     120
tctctaagga agaagtcaga cctccgagtg attcagaagg ttccatacaa aggtctcaaa     180
gattttctca ccaatctcca agaagtcatc ctcggcacta agctcgccat tcttttcccg     240
gccattcctg ccgccattat ctgcacctat tgtggcgtca gtcagccgtg atatttgga      300 ctgagcatgc taggactgac acctttggct gaacgagtca gctttctgac agagcaacta     360
gctttctaca ccggtccaac attgggtggt ctactgaacg caacgtgtgg aaacgcgact     420
gaattgataa ttgcgattct ggcattgacc aataataagg tcgcagtggt gaaatattcg     480
ctgttaggtt cgattttgtc aaatcttctt ttagttctag ggacttcact tctctgcggc     540
ggaatcgcta atatcaggag ggagcggcgg ttcgaccgga aacaagcgga tgtgaacttc     600
ttcttactcc taatgggttt gttgtgtcac ttgctcccat tgatgttcgt atacgtggca     660
```

-continued

```
accgcagaga ctccggctgc tcttgtttct gacatgacac tgactctgtc gcggggcagc        720 agtatttta tgttgatcgg ttacattgca tatctcgttt tccagctttg gtctcaccgc         780
caattgttcg acgcacaaga tcaggaagat gagtatgatg acgatgtaga ggaagaaacc        840
gcggtgatta gttttggag cggttttgct tggttggttg ggatgaccct tgtcatcgca         900
ttgctatccg agtatgttgt tgccaccatt gagaccgcat cggaatcatg gaacctatca        960
gtaagtttca taagcatcat attgcttccc attgttggaa atgcggctga acacgctgga       1020
gccatcattt ttgcctttaa gaacaagctc gacatatcat tggagttgc attaggctct        1080 gcgactcaga ttggcttatt cgtcgtaccc ttgaccataa tcgtggcgtg gattctagga       1140
attaatatgg atcttaactt caatctcctc gaaaccggtt ctcttgctct ttccattatc       1200
atcactgcct tcacattaca ggatgggact tcacactaca tgaagggact ggtcctcttg       1260
ctttgctatt tcattattgc cttctgtttc ttcgtcgaca aacttcctca gaaacaacca       1320
aatggttttc acatgggact tcaacagata aacaatgttg tcactggaat cactggaaca       1380
ggaggagctt cttcaactta a                                                 1401
```

<210> SEQ ID NO 15
<211> LENGTH: 1686
<212> TYPE: DNA
<213> ORGANISM: Caenorhabditis elegans

<400> SEQUENCE: 15

```
atggaagtaa caatggaaga tcgctctgtc aaagctgata aggctgatag agatgataac         60
aatactacct ccaccgaact gcttggtaaa atgcgtcaaa caaaagtgat cagtacaaac        120
caaaacaata atcatttgat tgatcgtatg gtgtcaatat atgagatgga aatgatcaaa        180
tcccaatcca cagaaactat cagcgatgta tcagacgttt tagaatttac ggttatcgat        240
aattgttcac acgtacaca tactcttgaa catgatctca ggcttaaagg agagcctatt        300
ggcaagtcgg aatctgttaa aggtgttagc agaagcctta ttattcaaat tgggatgact        360
gtgatattct gcgcacttga attcatcacg ggagtcgtct gttcatctat tgcaatgctt        420
gctgacagtt accatatggc agccgacgtg atggcgctca ttgtggcatt cacgtgcatt        480
aaaatcgcta ctcgcccttc cacgcgcctc ggatacggct gggtccgtgc tgaaacactt        540
ggaggattct tcaacggaat ctttatgtgt acggtatgtg ttctcgtgtt tcaagaggca        600
gttggacgta tcatcaatgt acacatgatt acacaccctc tacaagtact tgtcatcgga        660
ttcatcggat tgctaatcaa cttattcggt atgttcaact tgagtggtca cggtcacagt        720
catggaggcg gaagtcatgg tcacagtcac ggaggaagtc atggtcacag tcacaataac        780
aagaagacta agaaaaatga tgggcatggt cacagtcatg caaatggcca tggacactct        840
catgatggga aaagtgattg caatggtgaa gaagagccgg atcacactag attgaatgga        900
aaatttcgaa gtgcttctgc gatggcaaac tccgacgcca atgtgcgact actggataat        960
gatgacaact ccaatgacat tattgaacgt cgtctttctg gagttaatag tcagaatacc       1020
atcatcgcga cggtcgatcg tcaaatgaca ccatatggaa cacacatggc cagtgaagtt       1080
ctcaatgtgt cttctaacaa tctcgataaa agtgctcaaa agacagaaca gaaaaaagac       1140
aaaaatgtga acattcacgg agtttggctt catttattgt cggatgcctt cggatctgtg       1200
atcgtcatga tttctgccgg atttgtatac tttttgccaa catggaaaat tgccgcttat       1260
ttggatccaa ttttaagtat ttccctggcc tccatcatgg gtttcactgc agtggttctt       1320
```

| | |
|---|---:|
| gtcaaaacat cgggagaaaa gctgctcaag caaaccccag aagggctcga cctcgaaaag | 1380 |
| gtgaaaaaag atttgtgcag cattgttggt gtatccaaag tggaaaagct gtctgtgtgg | 1440 |
| acgttgtgtg ggcaacgaat cattgctgcc gcccacgtga acatatgtca cccagcagtt | 1500 |
| tttcctgaag ctgcttataa aattaaaaat tatttccacg acttgggagt acactcaacg | 1560 |
| actattgaac ccacctttga ggataccctgc atgcagtcga tgagaataat ggttaaaaaa | 1620 |
| gttgttgatg gcaaaagcat cgaggagcca gtcagtgtgt caactgaaaa tgaaatcacc | 1680 |
| gaataa | 1686 |

<210> SEQ ID NO 16
<211> LENGTH: 1701
<212> TYPE: DNA
<213> ORGANISM: Phaseolus vulgaris

<400> SEQUENCE: 16

| | |
|---|---:|
| attttccaat tcgtactgg attcattgct ccctcttctc gtgtatttgg aagaggtgtt | 60 |
| ttggttgaag attcttgggc aatagcaagg aggtatctat catcatattt cttagttgac | 120 |
| attcttgctg ttcttcccct cccacaggtg gtgattctag ttatcattcc aaagatgagt | 180 |
| ggttttaaat cacttaatac caagaacttg ctgaaatttg ttgtcttctt ccaatatgtg | 240 |
| cctcgtttat tgcgggtcat tccattatat agagaagtta caagagcctc tggcattctc | 300 |
| actgaaactg cttgggctgg agctgcattt aatctatttc tttacatgct gcaagtcat | 360 |
| gttgttggtg cctttggta cttgttttct atagaacgag aaaccacatg ttggcaagaa | 420 |
| gcctgtcgaa gtaatacaac agtgtgtaac aaggcagata tgtattgtaa tgattattgg | 480 |
| ggtgggctga gcaaaatttc gacattcctg aatacttctt gcccaataca aaggaagat | 540 |
| aaaaatctct tgattttggg aatgttcctt gatgctcttc aatccggtgt tgtggagtca | 600 |
| agagattttc cacaaaaatt cttttactgc ttttggtggg gcttaaaaaa tttgagttct | 660 |
| cttggccaga acctgggaac aagtcctatg tttgggaaat atgctttgca gttttcattt | 720 |
| ctgtatctgg tttgggtatt ttcattcctc attggaaata tgcagacata tttgcagtca | 780 |
| acaaccacaa gattggagga gatgagagtg aagaggaggg atgcagaaca gtggatgtct | 840 |
| cacccgattg cttctgatgg cctgagagtc cgaatcagac gatatgagca gtacaaatgg | 900 |
| caagaaacca gaggcgtaga tgaagacaat ttggttcgta atcttcccaa ggatttaaga | 960 |
| agagacatta agcgacatct ttgtttggct ttgctaatga gagtgccaat gtttgagaaa | 1020 |
| atggatgaac aacttctgga tgcaatgtgt gaccgtctga gccggtgct gttcactgaa | 1080 |
| gaaagctaca ttgtgaggga aggagaccca gttgatgaga tgctgttcat aatgcgtggg | 1140 |
| aagttactga ccataacaac taacggtgga agaaccggtt tcttcaactc ggagtatctg | 1200 |
| aaagctggtg acttctgtgg agaggagctt ctgacgtggg ccttggatcc ccattcctca | 1260 |
| tccaaccttc ccacctcaac cagaacagtc caaactcttt cagaagtgga agccttcgcc | 1320 |
| ctcaaagccg atgacttgaa gttcgtggca tcacagtttc ggcgccttca cagtaagcag | 1380 |
| ctacgccaca ctttccggtt ctactcgcaa caatggcggt cgtgggctgc gtgcttcatc | 1440 |
| caagctgcat ggcggcgata cagtaagagg aagcttgaag aatccctggt tgaagacgag | 1500 |
| aatagactgc aaaatgtgtt ggctaaatca ggtggaagct cacctagcct tggtgctaca | 1560 |
| atatatgctt caaggtttgc tgcaaatgca cttacattgc tacgccgtaa tggtgcaaag | 1620 |
| aagggtaggg tggcagagag attacccccc atgcttttc agaagcctgc agaacctgat | 1680 |
| tttactgcgg atgaagaata a | 1701 |

<210> SEQ ID NO 17
<211> LENGTH: 1551
<212> TYPE: DNA
<213> ORGANISM: Glycine max

<400> SEQUENCE: 17

| | | | | | |
|---|---|---|---|---|---|
| atgtctggga | gccaccaaga | gcagccactg | ttagagaact | cgttcataga | agaagacgag | 60 |
| ccgcaagaaa | cagcttatga | ttcgtcggag | aagatagtgg | tggtcggagt | cgacgagttc | 120 |
| gatgacgagg | agaattgggg | gagagtgccc | cgattctcgt | ggaagaagct | atggctgttc | 180 |
| accgggccgg | gctttctgat | gagcatagcg | tttctggacc | ctggaaactt | agaggggac | 240 |
| cttcaggcgg | tgccattgc | agggtactca | ttgttgtggc | ttctgatgtg | gccacagca | 300 |
| atgggcctcc | tgatccagct | cctctcggca | cggctcggcg | tggccacagg | gaagcacctc | 360 |
| gccgagctct | gccgagagga | gtatcctccg | tgggcccgga | tagtgctctg | gatcatggcg | 420 |
| gaactcgctc | tcattggctc | cgatattcag | gaggttattg | ggagcgctat | tgcaatcagg | 480 |
| attcttagtc | atggggttgt | gcccctttgg | gctggggttg | tcattactgc | tcttgattgt | 540 |
| tttattttc | tctttcttga | aactatggt | gtgaggactt | tggaagcttt | ttttgctatt | 600 |
| ctcattggtg | tgatggcaat | ctcgttcgca | tggatgtttg | gtgaagccaa | gcccagtggc | 660 |
| aaggaacttc | ttcttggagt | tttgattcca | aaactcagct | ccaaaactat | acagcaggct | 720 |
| gttggagttg | tggggtgcct | tattatgcct | cacaatgtgt | tcttgcactc | tgctcttgtt | 780 |
| cagtcaaggc | aggttgaccg | cagcaagaaa | ggccgagttc | aagaagctct | taattattac | 840 |
| tcgatagagt | ccacccttgc | ccttgtagtt | tcctttatta | taaatatttt | tgtaacaaca | 900 |
| gtgtttgcta | agggatttta | tggctctgaa | cttgcaaaca | gcataggtct | tgtaaatgca | 960 |
| ggacagtatc | tagaggagac | atatgggggt | ggactatttc | caattttata | catatggggt | 1020 |
| attggattat | tagcagcagg | ccaaagtagc | actattactg | ggacttatgc | aggacaattc | 1080 |
| atcatgggag | gttttctaaa | tttaaggtta | agaagtgga | tgaggcgtt | gattacccga | 1140 |
| agttgtgcaa | taattccaac | tatgatagtt | gctcttttat | tcgatacctc | ggaggaatcg | 1200 |
| ttagatgttt | tgaatgagtg | gcttaatgtt | cttcagtcag | tccagatccc | ctttgcactt | 1260 |
| attcccttgc | tttgtctggt | gtcaaaggag | cagataatgg | gcactttcag | aattggtgct | 1320 |
| gtcctcaaga | ctacttcatg | gctcgtggct | gctctggtga | tagtgattaa | tggctatctt | 1380 |
| ttgacggaat | tcttttcctc | tgaagtgaat | ggaccaatga | ttggcactgt | agtgggtgta | 1440 |
| ataactgctg | catatgttgc | cttcgtagta | taccttattt | ggcaagccat | cacctattta | 1500 |
| ccttggcaaa | gtgtaacaca | accaaagaca | attgctcatt | cagagggttg | a | 1551 |

<210> SEQ ID NO 18
<211> LENGTH: 1053
<212> TYPE: DNA
<213> ORGANISM: Lycopersicon esculentum

<400> SEQUENCE: 18

| | | | | | |
|---|---|---|---|---|---|
| atggcaaatt | ataatttcaa | gtacatcgcc | attttcctcc | ttctcatctc | aattttggcc | 60 |
| cctcgagtac | tatcagtagt | agaagattgt | ggagcagaag | aagacaactc | atgtgtcaat | 120 |
| aaatccaaag | cgttacccctt | aaaaatcata | gccatagtct | ccatccttat | cactagtatg | 180 |
| atcggagtat | gtcttccact | agtcacacgt | tctattccgg | ccctaagccc | ggaaagaaac | 240 |
| cttttttgtga | tagttaaggc | atttgctgct | ggaattatcc | tggctacggg | gtttatgcac | 300 |

-continued

```
gtgctaccgg actcgtttga catgttgtca tcgagttgcc ttaaggagca cccgtggcac        360
aaattcccct ttactggatt tgtggcaatg ttgtccgcta tagtaacgat ggctattgac        420
tctatagcta ctagtttata cagcaaaaag cataatggtg gtgtggttaa tccagaaggt        480
gatcaagaaa tggctgtggc tggaaatcat gttcattccc atcatcatca tggatccctt        540
tcgactaaag atggacttga tggcaaaaaa ttactaagat acagagtaat tgccatggtg        600
ttagagcttg gaattattgt tcactccata gtgattgggc tatcactagg tgcgtcaagc        660
aatacatgta cgattaaagg actcgtagct gcactttgct ttcatcaaat gtttgaagga        720
atgggccttg gtggttgcat cctacaggcg gagtataagt tcatgaagaa ggctataatg        780 gcgttttttct tcgcagtaac aacaccattt ggtatagcac ttgggatagc attgtcaact        840
acttatgagg aaaatagtcc acgggcgtta ataactgttg gattactgaa tgcatcatct        900
gctggacttt tgatatatat ggctttggtt gatcttcttg ctgctgattt tatgggtgac        960
aaattacaag gcagtgtcaa actacaaatt aagtcttaca tggctgttct tcttggtgct        1020
ggtggaatgt cagtcatggc catttgggct taa                                    1053
```

<210> SEQ ID NO 19
<211> LENGTH: 1059
<212> TYPE: DNA
<213> ORGANISM: Lycopersicon esculentum

<400> SEQUENCE: 19

```
atgagtgatt ataatttcaa gcacatcgcc atcatcttta ttctcatatc aattttcatc         60
cctcgagttt tatcagtagt agaagattgt ggagcgcaag aagataactc atgtgtcaac        120
aaatccaaag cgttacccct aaaaatcata gccatagtct ccatccttat cactagtatg        180
atcggagttt gtcttccact agtcacacgt tctatcccgg ccctaagccc ggaaagaaac        240 cttttttgtga tagtcaaggc atttgctgcc ggaattatat ggctacgggg gtttatgcac        300
gtgcttcctg actcattcga catgttgtca tcgagttgcc ttaaggagaa tccatggcac        360
aaattcccct tcactggatt tgttgctatg ttgtccgcta tagttacaat ggctattgac        420
tctatagcaa ctagtatgta tagcaaaaaa catagagctg gtttggttaa tccagaaact        480
ggtggtgctg atcaagaaat gggtgcagta aatggtggac attcacatca tcatcatgga        540
tcactttcca ctaaagacgg agttgaaggc actaaattac tacgatatag agtcatcgct        600
atggtgttag agctgggaat catagttcac tcaatagtaa taggaatttc acttggagct        660
tcaaacaata catgtacaat taaggattg gttgctgcac tttgctttca tcaaatgttt        720
gaaggaatgg gacttggtgg ttgcattctc caggctgagt acaagttttt gaagaagaca        780
ctaatggcat ttttcttcgc agtaacaact ccatttggta tagcacttgg tatggcattg        840
tcaactactt atgaggaaac tagcccacgg gcgttaataa ctgttggatt actgaatgca        900
tcatctgctg gcttttgat ttatatggct ttggttgatc ttcttgctgc tgattttatg        960
ggtgacaaat tacaaggcag tgtcaaacta caaattaagt cttacatggc tgttcttta        1020 ggtgctggtg gaatgtctct catggccaaa tgggcctag                               1059
```

<210> SEQ ID NO 20
<211> LENGTH: 1707
<212> TYPE: DNA
<213> ORGANISM: Mus musculus

<400> SEQUENCE: 20

```
atggtgttgg atcctaaaga aaagatgcca gacgatggcg cttctgggga ccatggagac         60
```

```
tctgccagcc ttggcgccat caaccctgcc tacagcaact catccctccc acattccact      120
ggagactctg aggagccctt caccacctac tttgatgaga aaatccccat tcctgaggag      180
gagtactctt gttttagctt tcgtaaactc tgggcgttca cggggcctgg ctttcttatg      240
agcattgcct acctagaccc aggaaacatc gaatctgatt tgcagtctgg agcagtggct      300
ggatttaagc tgctctgggt gctcctcttg gccaccattg tggggctgct gctccagcgc      360
cttgcagcga gacttggagt ggtcaccggc ttgcatcttg ctgaagtatg tcaccgtcag      420
tatcccaagg tcccacggat catcctgtgg ctgatggtgg agttggcaat cattggttct      480
gacatgcagg aagtcattgg ctcagccatc gccatcaatc tcctgtctgc aggaagggtc      540
cctgtgtggg gcgagtcct catcaccatc gcagacactt ttgtgtttct ttttttggac      600
aaatatggct tgcggaagct ggaagcgttt tttggctttc tcatcactat catggccctc      660
acgtttggat atgagtacat tacagtgaag cccagccaga gccaagtact caggggcatg      720
ttcgtgccgt cctgtccagg gtgccgcacc cctcaggtgg agcaggcggt gggcatcgtg      780
ggagctgtga tcatgccgca caacatgtac ctgcattctg ccttagtcaa gtctagacag      840
gtgaatcggg ccaataagca ggaagtgcgg gaagccaata agtacttctt catcgagtcc      900
tgcatcgcgc tctttgtttc cttcatcatc aatgtctttg tcgtgtccgt ctttgctgaa      960
gcattttttg agaaaaccaa caagcaggtg gttgaagtct gcaaaaataa cagcagcccc     1020
catgctgacc tctttcccag tgacaactct actctggctg tggacatcta caaaggggt     1080 gttgtgcttg gatgttactt cgggcctgca gctctctaca tctgggcagt ggggatcctg     1140
gctgccggtc agagctccac catgactgga acctattctg ccagtttgt catggaggga     1200 ttcctgaacc taaaatggtc gcgctttgcc cgagtgatcc tgacccggtc tatcgccatc     1260
atccccaccc tgctcgtcgc tgtcttccag gatgtggagc acctaacggg gatgaatgac     1320
ttcctgaatg tcctgcagag cttacagctc cccttgctc tcatacccat cctcacgttc     1380
acaagcctgc ggccagtgat gagtgagtt tccaatggaa taggctggag gattgccggt     1440
ggcatcctgg tcctgatcgt ctgctccatc aacatgtact ttgtagtggt ttatgtccag     1500
gagctagggc atgtggcact ctatgtggtg gctgcagtgg ttagcgtggc ttatttgacc     1560
tttgtgttct acttggggttg gcagtgtttg attgcattgg gtctgtcttt cctggactgt     1620
ggacgctcgt accgcctggg actgaccgct cagcctgaac tctatcttct gaacaccgtg     1680
gatgctgact cagtggtgtc cagatga                                         1707
```

<210> SEQ ID NO 21
<211> LENGTH: 1083
<212> TYPE: DNA
<213> ORGANISM: Medicago trunculata

<400> SEQUENCE: 21

```
atggaagtgg gggtgtcctt caaatgcacg gcttattcag taactataca caaagcaatc       60
ttcattgttt tcatcttaat cactttttta acatcacaag ccctagctga ttgtgaaagt      120
gaatccacaa acagttgcaa caacaaagaa aaggctcagc ctctaaaact catagccata      180
ttctcaatct tagcaactag tgtgattggt gtgtgtttac ccttggcgac acgttcaatc      240
ccggctttaa gcccagaagg agatcttttc ataatcgtga aatgtttcgc ggctggtatt      300
attcttggga ccgggttcat gcatgtactc cctgattcgt acgagatgtt gtggagtgat      360
tgtttagatg agaaaccatg gcacgagttt cccttttcgg gacttgtggc tatgttctcc      420
```

```
gcggtggtca caatgatggt cgattctata gctactagtt attatagtaa gaagggtaag      480
agcggagttg tgattccaga gagccatggt ggagatgatc aagagattgg acattcacat      540
ggtggtcacc atcatattca taatgggttc aagacagaag aaagtgacga gccacaactt      600
ctacgttatc gcgtagtggt catggtatta gaacttggaa ttgtagttca ttcagtggtg      660
ataggacttg gaatgggagc tccaataat acgtgctcaa taaaaggtat cttatcagca       720
gccttgtgct tccatcaaat gtttgaaggc atgggtcttg gtggctgcat tctccaggca     780
aagtacaagt tcttaaagaa tgcaatgttg gtattcttct tctcaattac aacaccactt     840
ggaattgcaa taggacttgc catgtcaaca agttacaaag agaatagtcc agtagcacta     900
atcaccgttg gattgcttaa tgcatcatct gctggtcttt taatctacat ggctttggtt    960
gacttattag ctgctgattt catgagtaag aggatgcaga gtagtattaa gcttcaatta     1020
aaatcttatg tagcagtatt ccttggtgct ggtggaatgt ctctcatggc taaatgggct    1080
taa                                                                    1083

<210> SEQ ID NO 22
<211> LENGTH: 1395
<212> TYPE: DNA
<213> ORGANISM: Oriza sativa

<400> SEQUENCE: 22
atgcgcccgg ccttctcgtg gcgcaagctg tggcggttca cggggcccgg gttcctcatg      60
tgcatcgcgt cctcgacccc ggggaacctg gagggcgacc tgcaggccgg cgccgcggcg     120
gggtaccagc tgctgtggct gctgctgtgg gcgacggtca tgggcgccct ggtgcagctg     180
ctctccgcgc ggctcggggt cgccacgggg aagcacctcg ccgagctctg cagggaggag     240
tacccgccct gggccacggc cgcgctctgg gccatgaccg agctcgcgct cgtcggcgcg     300
gacatccagg aggtgattgg cagcgcgatt gccatcaaga tcctctccgc tggcaccgtc     360
ccgctctggg gcggcgtcgt catcaccgcg ttcgattgct tcatcttttt attcctggag     420
aactatggag tgagaaaatt ggaagcattt ttcggagtcc tgattgcagt catggcagta     480
tcatttgcaa ttatgtttgg tgaaacaaag ccaagtggca aggaccttct gattggtttg    540
gtggttccaa agttgagttc aaggacaatc aaacaagcag ttggaattgt gggctgcata    600
atcatgcccc acaatgtctt cttgcactca gcactagtcg agtcaaggaa gattgacaca     660
aacaagaaat cccgtgttca agaagcagtg ttctattaca acattgagtc cattcttgcc     720
ctcgttgttt cgttctttat taacatctgt gtcacaacag ttttttgcgaa aggatttttat    780 ggatctgaac aagctgatgg tataggtctt gagaatgctg acagtactt acagcagaaa    840 tatgggactg cattctttcc tatactgtat atctgggcta ttgggctgtt agcatctgga    900
cagagtagca ctattactgg cacatatgca ggccaatttg ttatgggagg cttccttaat    960
cttcggttga gaagtggtt aagagcaatg attactcgaa gctttgcaat tattccaact     1020
atgattgtgg cttttatttt tgacacggag gatcctacaa tggacattct gaatgaggca     1080
ctcaatgttc ttcaatccat acagatacca tttgcactga ttcctctcat cacactcgtc    1140
tcaaaggagc aagtcatggg atcatttgtg gttggtccta tcacaaaagt gattagctgg    1200
attgttacag tattccttgat gctcatcaat gggtatctta tactgtcctt ctatgccact    1260
gaagtccggg gagcattggt tcggtcaagc ttgtgcgttg tattggcagt ttaccttgca    1320
ttcatcgtct atcttatcat gcaaaatacc tcactgtatt ctcgcctccg ctcagcaatg    1380
acaaagagca catga                                                     1395
```

<210> SEQ ID NO 23
<211> LENGTH: 1047
<212> TYPE: DNA
<213> ORGANISM: pisum sativum

<400> SEQUENCE: 23

| | | | | | |
|---|---|---|---|---|---|
| atggctaatc | cagtaactaa | acaaaaatta | atctccattg | tgtttatctt | aatcactctt | 60 |
| ttcacatcac | aagccctagc | tgattgtgaa | accgaaagca | caaacagttg | taacaacaaa | 120 |
| gaaaaggctc | tgtctcttaa | aatcatagca | atattctcaa | tattagtaac | tagcatgatt | 180 |
| ggagtgtgtc | tacccttggt | gtcacgttcc | gtcccggctt | aagcccgga | cggaaatctg | 240 |
| ttcgtgatcg | tgaagtgttt | cgcggccggt | atcattcttg | gaactgggtt | catgcatgta | 300 |
| cttcctgatt | cgttcgacat | gttgtggtcg | gattgtttgc | aggagaaacc | gtggcacgag | 360 |
| tttccgtttt | cgggatttgc | ggctatgatc | tctgcggtgg | ttacaatgat | ggtggattct | 420 |
| ctggctacta | gctattatac | tcagaagggt | aagaaaggtg | ttataattcc | agctgaaggt | 480 |
| gaagttggag | atcaagagat | gggtgctgtc | catgctggtc | accatcacca | ttaccaggtg | 540 |
| aagacggaag | gcgaggagtc | acagcttctc | cgttatcgtg | taatcgccat | ggtattagaa | 600 |
| ctcggaatag | tagttcattc | gatcgtgata | ggacttgcca | tgggatcctc | caataacaca | 660 |
| tgctcgataa | aaggtctagt | tgcggcactt | tgcttccatc | aaatgttcga | aggcatgggt | 720 |
| cttggtggtt | gcatcctcca | ggcggagtac | aagtttgtaa | agaaggctat | aatggtgttt | 780 |
| ttcttctcaa | taacaacacc | acttggaatt | gcaatagga | ttgcaatgtc | tagtaattac | 840 |
| aaagagaaca | gtccaaaagc | attaatcact | gttggattgc | ttaatggatc | atctgctggt | 900 |
| cttttaatct | acatggcttt | ggttgatctt | cttgctgctg | atttcatgag | taggaggatg | 960 |
| cagggtagta | ttaaacttca | attaaaatct | tatgttgctg | tgtttcttgg | tgctggtggc | 1020 |
| atgtctctca | tggctaaatg | ggcttga | | | | 1047 |

<210> SEQ ID NO 24
<211> LENGTH: 1044
<212> TYPE: DNA
<213> ORGANISM: Thlaspi caerulescens

<400> SEQUENCE: 24

| | | | | | |
|---|---|---|---|---|---|
| atggcttcaa | cttcaacact | tctcatgaaa | acaatcttcc | tcgtactcat | ctttgtctct | 60 |
| tttgcaatct | ctcctgcaac | ttcaacggcg | ccggatgatt | gtgcaagcga | gtcagcgaac | 120 |
| ccgtgcgtca | acaaagctaa | agctttgcct | ctcaaaatca | tagcaatcgc | cgcaatccta | 180 |
| gttgcaagca | tgattggtgt | tggagctcct | cttttttagcc | gctccgtgcc | gttccttcaa | 240 |
| cccgacggga | acattttcac | catcgttaag | tgtttcgcct | cagggattat | ccttggaacc | 300 |
| gggtttatgc | acgttttgcc | tgattcgttc | gatatgttgt | catctaaatg | tcttggagag | 360 |
| aacccgtggc | acaaatttcc | cttctccgga | tttctcgcta | tgttggcctg | tctagtgact | 420 |
| ctagtcatcg | attccatggc | tacaaccctc | tatactagca | agaacgtagt | ggggatcgta | 480 |
| ccccatggtc | atggtcatgg | tcatggcccc | gaaaatgatg | ttgccttacc | aataaaagaa | 540 |
| gatgattccg | cgaatgcaca | actcttgcga | tatcgagtca | ttgctatggt | attggaactt | 600 |
| ggaattatag | ttcactctgt | ggtcattgga | ctatctctag | agcaacaag | tgacacttgt | 660 |
| accattaaag | gactcatcgc | agctcttttgt | ttccatcaaa | tgttcgaagg | catgggtctt | 720 |
| ggcggttgca | tcctccaggc | tgagtatacg | aacatgaaaa | agtttgttgt | ggccttcttt | 780 |

| | |
|---|---:|
| tttgcggtaa caacgccttc cggaatagca ttagggattg ctctttcgac cgtttacaga | 840 |
| gaaaatagtc cctctgcatt gatcactgtt gggttactca atgcatgctc tgcgggattg | 900 |
| ctcatctaca tggcgcttgt cgaccttcta gcggccgagt tcatgggacc aaagcttaaa | 960 |
| ggtagcatca aaatgcaggc caagtgtttc cttgcagctc ttctcgggtg cggtggcatg | 1020 |
| tcgatcatcg ccaaatgggc ttaa | 1044 |

```
<210> SEQ ID NO 25
<211> LENGTH: 399
<212> TYPE: DNA
<213> ORGANISM: Thlaspi caerulescens

<400> SEQUENCE: 25
```

| | |
|---|---:|
| gtgtcattgc catggttagt gtccayatgg aaataatttg agacggccgt taaattcgac | 60 |
| gtagcatttt aattaaaatc atttaccaaa gtaaaccatt ttttgaatt tcttgaatag | 120 |
| gtattggagc ttgggatttt atttcattct gtggtcattg gactatctct aggagcaact | 180 |
| aatgatgcat gtaccattaa aggactcatc atagctcttt gcttccatca cttgttcgaa | 240 |
| ggcataggtc tcggtggctg catcctccag gtaccaatat acattcatac tatatatata | 300 |
| gtttatgtct cttctatcaa ttagaaatat acgctcattt gtatatataa tttatgtgaa | 360 |
| acaggcagat tttacaaatg tgaagaagtt ctcgatggc | 399 |

```
<210> SEQ ID NO 26
<211> LENGTH: 1539
<212> TYPE: DNA
<213> ORGANISM: Thlaspi caerulescens

<400> SEQUENCE: 26
```

| | |
|---|---:|
| atgtcacggc tcgagaacga tcgtccgctt ctcatcgaca gaatcgacga ggaagaagaa | 60 |
| gagacggcgt acgacgaaac agagaaagtt cacatcgtga gagacgaaga cgacaacgag | 120 |
| agggatctcg agtacggcgt cggatgcggc ggcgcgccgc cgttctcgtg gaggaagtta | 180 |
| tggctattca ccggacctgg attcctgatg agcattgcgt ttctcgaccc agggaacctc | 240 |
| gaaggagatc tccaatccgg tgctgtcgcc ggatactcgc ttctctggtt gctcatgtgg | 300 |
| gcaacggcga tgggacttct ggttcagctt ctctcggcga gctcggcgt cgcgacgggt | 360 |
| cgtcacttgg cggagctttg ccgggaagag tatccgagtt gggcgggtat ggttttgtgg | 420 |
| gttatgcgg aattggcttt gatcggatct gatattcagg aagtgatcgg aagtgcgatt | 480 |
| gctattaaga ttttgactaa tgggattttg cctctctggg ctggtgtcat catcactgct | 540 |
| cttgactgtt tcttcttctt gttctttgag aactacggaa taaggaagct cgaggcagtg | 600 |
| tttgcggttt tgatcgctac aatggagtc tcattcgctt gatgtttgg tcaagccaag | 660 |
| ccaagtggct ctgagcttct cgttggcata ttggtaccga aactgagctc aagaacgata | 720 |
| caaaaagcag taggagttgt gggttgtatt ataatgccgc acaacgtgtt tcttcactca | 780 |
| gctcttgttc agtctcgaga agtcgacaaa cggcagaaat acagagtcca agaagctata | 840 |
| aactactaca caatcgaatc cacgctcgct ctcttcgtct cctttctgat caatctcttt | 900 |
| gtcacgacgg ttttcgctaa agggttttac aacactgact agccgatag cattggcctt | 960 |
| gtaaacgccg gacagtatct tcaggacaag tatgaggcg gcttgttccc gatactgtac | 1020 |
| atttggggaa tcggtttatt agctgcggga cagagcagta ccattacagg tacttacgca | 1080 |
| ggacaattca tcatgggagg gttctttaat ttcagaatga gaaatggat gagagctttg | 1140 |
| atcacacgaa gctgcgcgat cattccaacg atcatcgttg cgctagtgtt tgattcatcg | 1200 |

-continued

```
gaagctacac tcgatgtctt gaacgagtgg cttaacgtgc ttcaatcaat tcaaatccct      1260
tttgctctca tcccattgct ctgtttggtt tccaaggaac gaatcatggg tagtttcaaa      1320
atcggtcctt tgtgtcagac aatcgcgtgg ctagtcgctg cgctcgtgat catgatcaac      1380
ggctatcttt tggttgagtt tttctcatcg gaggttagtg gcatcgtcta caccggtttt      1440
gtgattgtgt tcacggcttc gtatggtgca ttcatagtct acctcattgc tcgtggcatc      1500
aatttcactc cgtggcgtcc taaagcagag tctagttga                            1539
```

<210> SEQ ID NO 27
<211> LENGTH: 1533
<212> TYPE: DNA
<213> ORGANISM: Thlaspi japonicum

<400> SEQUENCE: 27

```
atgtcggagt cggagagagc gcgtccattt ttagaatcgg aggagaaagc ttttgaagaa       60
actgacaagg ttcacgttgt cggagtcgac gaagatgatg acgtcggtta cgacgagctc      120
ggaaatgcgc ctccgttctc atggaagaag ctttggctgt tcaccggacc tggctttctg      180
atgagcatcg ccttcctcga tcccggtaac ctcgagagcg atctccaagc cggagccatc      240
gctggttact ctctgatttg gctcttgatg tgggcgacgg cgatcgggct tctgattcag      300
cttctctctg ctcgtctcgg cgtcgccacc ggccgacacc tggcggagct gtgtcgggaa      360
gagtatccga cttgggccag gatggtgctt tggatcatgg cggagattgc tttgatcggt      420
gccgatattc aggaagtcat cggaagtgcc atagctatca agatcttgtc taatggattg      480
atccctctct gggctggtgt tgtaatcact gctctcgatt gtttcatatt tctaattctg      540
gagaattacg gagtaaggaa actagaagct gtgtttgctg ttttgattgc aacaatggcg      600
ctttcatttg cttggatgtt tggccagaca aagcctagtg gaaccgaact tcttgttgga      660
gctttggtcc caaaactaag ctccaggact ataaaacaag ctgttggaat tgtgggatgc      720
atcatcatgc ctcacaatgt gtacttgcac tcagcgcttg tgcaatcgag agaaatcgat      780
ccgaaaaaga gattccgtgt caaagaagcc ctcaggtact attccattga atccaccgga      840
gctctcgtgg tttccttcat aatcaacgtc tgtgtgacca ccgtgtttgc taaatctttc      900
tataagacag acatagcgga tactatcggt cttgcaaacg caggagatta cttacaggaa      960
aaatacggcg gcggatattt tccggtgtac tatatatggg ccgtcggact tttagctgct     1020
ggtcagagta gtaccatcac tggtacatac gccggacagt ttataatggg agggttcttg     1080
aatctcaaga tgaagaaatg gattagagcg acaatcacaa gaagctgcgc gatcatccct     1140
acgatgatcg tggcgattgt ctttaattct tcggctacat tgctcgacga gctcaacgaa     1200
tggctaaacg ttcttcagtc tgttcagatc cctttcgctg tgatccctct cctttgcttg     1260
gtctccaacg agaggatcat gggcagcttc aaaatcaaac ctttaatgca ggcaatctcg     1320
tggcttgtag ctgctcttgt gatagccatt aacgcgtatc tgatggtaaa tttcttctcg     1380
ggagctgcga agagtgtggt catgctcgtg cttgtgatca tattcgttgt tgcgtatgtt     1440 tttttgtgc tttaccttat ctcaagaggc ttcacgtaca ctccctggca gttagtggct     1500
tcggagaaag taaagagag ggatgatgag taa                                   1533
```